United States Patent
Malamas et al.

(10) Patent No.: US 6,232,322 B1
(45) Date of Patent: *May 15, 2001

(54) BIPHENYL OXO-ACETIC ACIDS USEFUL IN THE TREATMENT OF INSULIN RESISTANCE AND HYPERGLYCEMIA

(75) Inventors: Michael S. Malamas, Jamison, PA (US); Robert E. McDevitt, Somerset; Folake O. Adebayo, Cranbury, both of NJ (US)

(73) Assignee: American Home Products Corporation, Madison, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/307,972

(22) Filed: May 10, 1999

Related U.S. Application Data
(60) Provisional application No. 60/113,654, filed on May 12, 1998.

(51) Int. Cl.⁷ .................... A61K 31/343; A61K 31/437; C07D 307/79; C07D 333/52; C07D 471/06

(52) U.S. Cl. .................... 514/303; 514/443; 514/469; 546/118; 549/49; 549/58; 549/469

(58) Field of Search .................... 514/303, 340, 514/367, 375, 394, 443, 469; 546/118; 548/165, 170, 186, 217, 235, 305.1, 311.1; 549/58, 49, 78, 469, 483

(56) References Cited

U.S. PATENT DOCUMENTS

| | | |
|---|---|---|
| 3,666,473 | 5/1972 | Colom . |
| 4,117,151 | 9/1978 | Deschamps et al. . |
| 4,808,599 | 2/1989 | Dubroeucq et al. . |
| 5,235,064 | 8/1993 | Gapinski . |
| 5,262,083 | * 11/1993 | Mori et al. . |
| 5,334,598 | 8/1994 | Bagley et al. . |
| 5,523,302 | 6/1996 | Cain et al. . |
| 5,596,106 | 1/1997 | Cullinan et al. . |
| 5,688,821 | 11/1997 | Kees . |
| 5,698,574 | 12/1997 | Riedl et al. . |

FOREIGN PATENT DOCUMENTS

| | | |
|---|---|---|
| 1249869 | 9/1967 | (DE) . |
| 1291197 | 3/1969 | (DE) . |
| 2616414 | 10/1977 | (DE) . |
| 3110460 | 12/1982 | (DE) . |
| 3342624 | 3/1984 | (DE) . |
| 0276064 | 7/1988 | (EP) . |
| 0449222 | 8/1992 | (EP) . |
| 0568289 | 11/1993 | (EP) . |
| 0693491 | 1/1996 | (EP) . |
| 0818453 | 1/1998 | (EP) . |
| 1293396 | 11/1969 | (GB) . |
| 58150948 | 9/1983 | (JP) . |
| 60172946 | 9/1985 | (JP) . |
| 62-36662 | 2/1987 | (JP) . |
| 6236661 | 2/1987 | (JP) . |
| 63-161449 | 7/1988 | (JP) . |
| 3247655 | 11/1991 | (JP) . |
| 4016854 | 1/1992 | (JP) . |
| 6348018 | 12/1994 | (JP) . |
| 9111909 | 8/1991 | (WO) . |
| 9117163 | 11/1991 | (WO) . |
| 9422834 | 10/1994 | (WO) . |
| 9422835 | 10/1994 | (WO) . |
| 9608483 | 3/1996 | (WO) . |
| 9609818 | 4/1996 | (WO) . |
| 9634851 | 11/1996 | (WO) . |
| 9716442 | 5/1997 | (WO) . |
| 9721435 | 6/1997 | (WO) . |
| 9721693 | 6/1997 | (WO) . |

OTHER PUBLICATIONS

Hamacher, H., Arch. Pharmaz. 308/75 pp. 290–301 (1995).
d'Ischia, M. et al., Tetrahedron, 43:2, 1987, pp. 431–434.
Dryhurst, G. et al., J. Am. Chem. Soc., 111, 1989, pp. 713–726.
Guirguis, N. R. et al., J. Prakt. Chemie, 332:3, 1990, pp. 414–418.
Guirguis, N. R. et al., Liebigs Ann. Chem., 1986, pp. 1003–1011.
Han, B. H. et al., Tetrahedron Leter, 31:8, 1990, pp. 1181–1182.
Hashem, A. I., J. Prakt. Chemie, 319:4, 1977, pp. 689–692.
Ahmad, F. et al., Biochemica et Biophysica Acta, 1248, 1995, pp. 57–69.
Chang, A.Y. et al., Diabetes, 32, 1983, pp. 830–838.
Coleman, D. L., Diabetologia, 14, 1978, pp. 141–148.
DeFronzo, R. A. et al., Diabetes Care, 14:3, 1991, pp. 173–194.
Goldstein, B. J., Receptor, 3, 1993, pp. 1–5.
Goldstein, B. J. et al., Mol. and Cell. Biochem., 109, 1992, pp. 107–113.

(List continued on next page.)

Primary Examiner—Joseph K. McKane
Assistant Examiner—Taofiq A. Solola
(74) Attorney, Agent, or Firm—Arnold S. Milowsky

(57) ABSTRACT

This invention provides compounds of Formula I having the structure

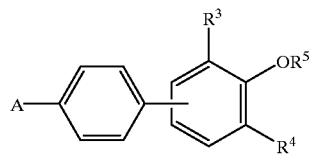

wherein A, $R^3$, $R^4$, and $R^5$ are as defined hereinbefore in the specification, or a pharmaceutically acceptable salt thereof, which are useful in treating metabolic disorders related to insulin resistance or hyperglycemia.

71 Claims, No Drawings

OTHER PUBLICATIONS

Napolitano, A. et al., Tetrahedron, 45:21, 1989, pp. 6749–6760.
Schuster, I. I., et al., J. Org. Chem., 53, 1988, pp. 5819–5825.
Buu–Hoi, N. P. et al., J. Chem. Soc., 1957, pp. 625–628.
Brown, E. V. et al., J. Med. Chem., 14:1, 1971, pp. 84–85.
Kimura, T. et al., Tetrahedron Letters, 36:7, 1995, pp. 1079–1080.
Massolini, G. et al., Il Farmaco, 45(2), 1990, pp. 263–268.
Miyaura, N. et al., Synthetic Communications, 11:7, 1981, pp. 513–519.
Barraclough, P. et al., Arch. Pharm., 323, 1990, pp. 507–512.
Liebeskind, L. S. et al., J. Org. Chem., 55, 1990, pp. 5359–5364.
Toth, I., Liebigs Ann. Chem., 1994, pp. 685–688.
Han, B. H. et al., Tetrahedron Letters, 31:8, 1990, pp. 1181–1182.
Mitsunobu, O., Synthesis, Jan. 1981, pp. 1–28.
Lefker, B. A. et al., Tetrahedron Letters, 35:29, 1994, pp. 5205–5208.
Kano, S. et al., Heterocycles, 19:6, 1982, pp. 1033–1037.
Martin, S.F. et al., J. Org. Chem., 49, 1984, pp. 2512–2513.
Eckert, T. et al., Arch. Pharm., 315, 1982, pp. 569–570.
Goldenberg, C. et al., Eur. J. Med. Chem., Chim. Ther., 12:1, Jan.–Feb. 1977, pp. 81–86.
Artini, D. et al., Arzneim–Forsch. (Drug Res.), 21:1, 1971, pp. 30–36.
Ayyangar, N.R. et al., Synthesis, Apr. 1991, pp. 322–324.
Darchen, A. et al., J.C.S. Chem. Comm., 1976, p. 820.
De Cointet, P. et al., Chimie Therapeutique, 5, Sep.–Oct. 1973, pp. 574–587.
Konopelski, J. P. et al., Synlett, Letters, Jul. 1996, pp. 609–611.
Kuroda, T. et al., J. Org. Chem., 59, 1994, pp. 7353–7357.
Kuroda, T. et al., J. Chem. Soc., Chem. Commun., 1991, pp. 1635–1636.
Lefker, B. A. et al., Tetrahedron Letters, 35:29, 1994, pp. 5205–5208.
Molina, P. et al., Tetrahedron, 50:17, 1994, pp. 5027–5036.
Molina, P. et al., Tetrahedron Letters, 34:17, 1993, pp. 2809–2812.
Goldstein, B. J., J. Cell. Biochem., 48, 1992, pp. 33–42.
Haring, H. U., Diabetologia, 34, 1991, pp. 848–861.
Harris, M. I. et al., Diabetes in America, 1985, Chapter 29, pp. 1–48.
Jarrett, R. J., Diabetes/Metabolism Reviews, 5:7, 1989, pp. 547–558.
Lanzetta, P. A. et al., Analytical Biochem. 100, 1979, pp. 95–97.
McGuire, M. C. et al., Diabetes, 40, Jul. 1991, pp. 939–942.
Meyerovitch, J. et al., J. Clin. Invest., 87, Apr. 1991, pp. 1286–1294.
Meyerovitch, J. et al., J. Clin. Invest., 84, Sep. 1989, pp. 976–983.
Mitsunobu, O., Synthesis, Jan. 1981, pp. 1–28.
Nutaitis, C.F., Organic Preparations and Procedures Int., 23(4), 1991, pp. 403–411.
Perich, J. W. et al., Synthesis, Feb. 1988, pp. 142–144.
Phillion, D. P. et al., Tetrahedron, 27:13, 1986, pp. 1477–1480.
Pyorala, K. et al., Diabetes/Metabolism Reviews, 3:2, 1987, pp. 463–524.
Reaven, G.M. et al., Amer. J. Med., 60, 1976, pp. 80–88.
Sredy, J. et al., Metabolism, 44:8, 1995, pp. 1074–1081.
Stout, R. W., Metabolism, 34:12 (Suppl 1), Dec. 1985, pp. 7–12.
Zask, A. et al., J. Med. Chem., 33, 1990, pp. 1418–1423.
Chen, H.–M. et al., Indian J. Chem., 35B, Dec. 1996, pp. 1304–1307.
Kauffman et al. J. Heterocycl. Chem., vol. 31(4), pp. 957–965, 1994.*

* cited by examiner

BIPHENYL OXO-ACETIC ACIDS USEFUL IN THE TREATMENT OF INSULIN RESISTANCE AND HYPERGLYCEMIA

This application claims the benefit of U.S. Provisional Application No. 60/113,654, which was converted from U.S. patent application Ser. No. 09/076,205, filed May 12, 1998, converted to Provisionnal Application No. 60/113,654 pursuant to a petition filed under 37 C.F.R. 1.53(c)(2)(i) on Nov. 24, 1998.

BACKGROUND OF THE INVENTION

The prevalence of insulin resistance in glucose intolerant subjects has long been recognized. Reaven et al (*American Journal of Medicine* 1976, 60, 80) used a continuous infusion of glucose and insulin (insulin/glucose clamp technique) and oral glucose tolerance tests to demonstrate that insulin resistance existed in a diverse group of nonobese, nonketotic subjects. These subjects ranged from borderline glucose tolerant to overt, fasting hyperglycemia. The diabetic groups in these studies included both insulin dependent (IDDM) and noninsulin dependent (NIDDM) subjects.

Coincident with sustained insulin resistance is the more easily determined hyperinsulinemia, which can be measured by accurate determination of circulating plasma insulin concentration in the plasma of subjects. Hyperinsulinemia can be present as a result of insulin resistance, such as is in obese and/or diabetic (NIDDM) subjects and/or glucose intolerant subjects, or in IDDM subjects, as a consequence of over injection of insulin compared with normal physiological release of the hormone by the endocrine pancreas.

The association of hyperinsulinemia with obesity and with ischemic diseases of the large blood vessels (e.g. atherosclerosis) has been well established by numerous experimental, clinical and epidemiological studies (summarized by Stout, *Metabolism* 1985, 34, 7, and in more detail by Pyorala et al, *Diabetes/Metabolism Reviews* 1987, 3, 463). Statistically significant plasma insulin elevations at 1 and 2 hours after oral glucose load correlates with an increased risk of coronary heart disease.

Since most of these studies actually excluded diabetic subjects, data relating the risk of atherosclerotic diseases to the diabetic condition are not as numerous, but point in the same direction as for nondiabetic subjects (Pyorala et al). However, the incidence of atherosclerotic diseases in morbidity and mortality statistics in the diabetic population exceeds that of the nondiabetic population (Pyorala et al; Jarrett *Diabetes/Metabolism Reviews* 1989,5, 547; Harris et al, Mortality from diabetes, in *Diabetes in America* 1985).

The independent risk factors obesity and hypertension for atherosclerotic diseases are also associated with insulin resistance. Using a combination of insulin/glucose clamps, tracer glucose infusion and indirect calorimetry, it has been demonstrated that the insulin resistance of essential hypertension is located in peripheral tissues (principally muscle) and correlates directly with the severity of hypertension (DeFronzo and Ferrannini, *Diabetes Care* 1991, 14, 173). In hypertension of the obese, insulin resistance generates hyperinsulinemia, which is recruited as a mechanism to limit further weight gain via thermogenesis, but insulin also increases renal sodium reabsorption and stimulates the sympathetic nervous system in kidneys, heart, and vasculature, creating hypertension.

It is now appreciated that insulin resistance is usually the result of a defect in the insulin receptor signaling system, at a site post binding of insulin to the receptor. Accumulated scientific evidence demonstrating insulin resistance in the major tissues which respond to insulin (muscle, liver, adipose), strongly suggests that a defect in insulin signal transduction resides at an early step in this cascade, specifically at the insulin receptor kinase activity, which appears to be diminished (reviewed by Haring, *Diabetalogia* 1991, 34, 848).

Protein-tyrosine phosphatases (PTPases) play an important role in the regulation of phosphorylation of proteins. The interaction of insulin with its receptor leads to phosphorylation of certain tyrosine molecules within the receptor protein, thus activating the receptor kinase. PTPases dephosphorylate the activated insulin receptor, attenuating the tyrosine kinase activity. PTPases can also modulate post-receptor signaling by catalyzing the dephosphorylation of cellular substrates of the insulin receptor kinase. The enzymes that appear most likely to closely associate with the insulin receptor and therefore, most likely to regulate the insulin receptor kinase activity, include PTP1B, LAR, PTPα and SH-PTP2 (B. J. Goldstein, *J. Cellular Biochemistry* 1992, 48, 33; B. *J. Goldstein, Receptor* 1993, 3, 1–15,; F. Ahlmad and B. J. Goldstein *Biochim. Biophys Acta* 1995, 1248, 57–69).

McGuire et al. (*Diabetes* 1991, 40, 939), demonstrated that nondiabetic glucose intolerant subjects possessed significantly elevated levels of PTPase activity in muscle tissue vs. normal subjects, and that insulin infusion failed to suppress PTPase activity as it did in insulin sensitive subjects.

Meyerovitch et al (*J. Clinical Invest*. 1989, 84, 976) observed significantly increased PTPase activity in the livers of two rodent models of IDDM, the genetically diabetic BB rat, and the STZ-induced diabetic rat. Sredy et al (*Metabolism*, 44, 1074, 1995) observed similar increased PTPase activity in the livers of obese, diabetic ob/ob mice, a genetic rodent model of NIDDM.

The compounds of this invention have been shown to inhibit PTPases derived from rat liver microsomes and human-derived recombinant PTPase-1B (hPTP-1B) in vitro. They are useful in the treatment of insulin resistance associated with obesity, glucose intolerance, diabetes mellitus, hypertension and ischemic diseases of the large and small blood vessels.

DESCRIPTION OF THE INVENTION

This invention provides a compound of formula I having the structure

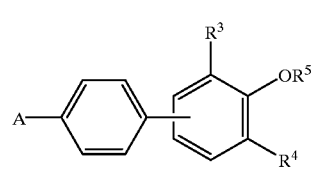

I wherein

A is

[chemical structure] or [chemical structure];

B is carbon or nitrogen;

D is oxygen, sulfur, or nitrogen;

E is carbon or nitrogen;

Y is a bond, methylene, C(O), or CH(OH);

$R^1$ is alkyl containing 1 to 12 carbons, aryl of 6–12 carbon atoms, arylalkyl of 7–15 carbon atoms, halogen, carboxaldehyde, trifluoromethyl, alkoxy of 1–6 carbon atoms, 2,2-dimethyl-1,3-benzodioxole, Het-alkyl wherein the alkyl moiety contains 1–6 carbon atoms, or aryl of 6–10 carbon atoms which is mono-, di-, or tri-substituted with halogen, trifluormethyl, or alkoxy of 1–6 carbon atoms;

Het is

[chemical structure];

G is oxygen, sulfur or nitrogen;

$R^2$ and $R^{2a}$ are each, independently, hydrogen, alkyl of 1–6 carbon atoms, alkoxy of 1–6 carbon atoms, halogen, trifluoromethyl;

$R^3$ and $R^4$ are each, independently, hydrogen, halogen, alkyl of 1–6 carbon atoms, aryl of 6–10 carbon atoms, trifluoromethyl, alkoxy of 1–6 carbon atoms, nitro, amino, carboalkoxy, carbamide, carbamate, urea, alkylsulfoamide, arylsulfoamide, cycloalkyl of 3–8 carbon atoms, —NR$^7$(CH$_2$)$_m$CO$_2$H, pyrrolidinone, a heterocycic ring containing 5 to ring 7 atom rings having 1 to 3 heteroatoms selected from oxygen, nitrogen, or sulfur, or aryl of 6–10 carbon atoms mono-, di-, or tri-substituted with trifluoromethyl, alkyl of 1–6 carbon atoms or, alkoxy of 1–6 carbon atoms;

$R^5$ is hydrogen, alkyl of 1–6 carbon atoms, —CH(R$^8$)R$^9$, —C(CH$_2$)$_n$CO$_2$R$^{10}$, —C(CH$_3$)$_2$CO$_2$R$^{10}$, —CH(R$^8$)(CH$_2$)$_n$CO$_2$R$^{10}$, —CH(R$^8$)C$_6$H$_4$CO$_2$R$^{10}$ $R^6$ is alkylene of 1 to 3 carbon atoms $R^7$ is hydrogen or alkyl of 1 to 6 carbon atoms, $R^8$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety contains 1–6 carbon atoms;

Q is

[chemical structure], [chemical structure],

[chemical structure], or [chemical structure];

W is oxygen, sulfur, or nitrogen;

$R^9$ is —CO$_2$R$^{12}$, —CONHR$^{12}$, tetrazole, —PO$_3$R$^{12}$;

$R^{10}$ is hydrogen, alkyl of 1–6 carbon atoms, aryl of 7–15 carbon atoms, or aralkyl of 7–15 carbon atoms;

$R^{12}$ is hydrogen, alkyl, aryl of 6–12 carbon atoms, aralkyl of 7–15 carbon atoms;

m=1–3;

n=1–6;

with the proviso that when $R^1$ is halogen, Y is a bond;

or a pharmaceutically acceptable salt thereof, which are useful in treating metabolic disorders related to insulin resistance or hyperglycemia.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

Alkyl includes both straight chain as well as branched moieties. Halogen means bromine, chlorine, fluorine, and iodine. It is preferred that the aryl portion of the aryl or aralkyl substituent is a phenyl, naphthyl or 1,4-benzodioxan-5-yl group; with phenyl being most preferred. The aryl moiety may be optionally mono-, di-, or tri-substituted with a substituent selected from the group consisting of alkyl of 1–6 carbon atoms, alkoxy of 1–6 carbon atoms, trifluoromethyl, halogen, alkoxycarbonyl of 2–7 carbon atoms, alkylamnino of 1–6 carbon atoms, and dialkylamino in which each of the alkyl groups is of 1–6 carbon atoms, nitro, cyano, —CO$_2$H, alkylcarbonyloxy of 2–7 carbon atoms, and alkylcarbonyl of 2–7 carbon atoms.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

When A is

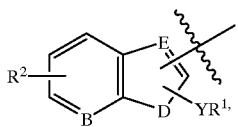

the following compounds of A are preferred:

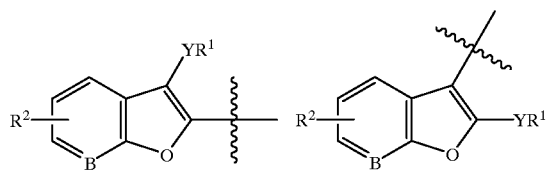

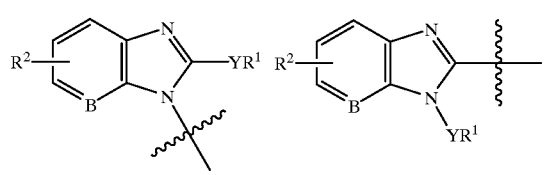

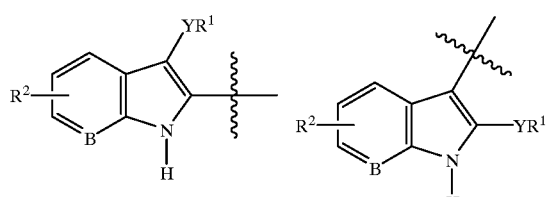

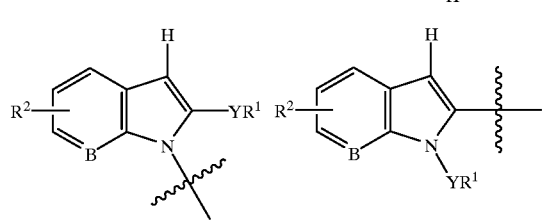

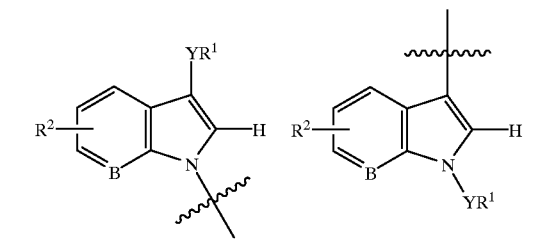

Preferred compounds of this invention are those compounds of Formula I, in which:

A is

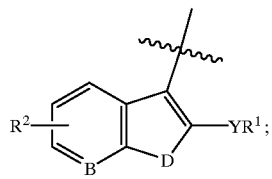

wherein
B is carbon or nitrogen;
D is oxygen or sulfur; or
A is

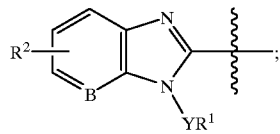

or
A is

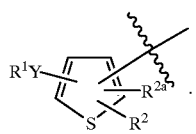

Specifically preferred compounds of the present invention are set forth below:

(4'-benzofuran-3-yl-biphenyl-4-yloxy)-acetic acid
2-(4'-benzofuran-3-yl-biphenyl-4-yloxy)-3-phenyl-propionic acid
[4'-(2-bromo-benzofuran-3-yl)-biphenyl-4-yloxy]-acetic acid
2-[4'-(2-bromo-benzofuran-3-yl)-biphenyl-4-yloxy]-3-phenyl-propionic acid
4'-(2-butyl-benzofuran-3-yl)-biphenyl-4-ol
[4'-(2-butyl-benzofuran-3-yl)-biphenyl-4-yloxy]-acetic acid
2-[4'-(2-butyl-benzofuran-3-yl)-biphenyl-4-yloxy]-3-phenyl-propionic acid
2-[4'-(2-benzyl-benzofuran-3-yl)-biphenyl-4-yloxy]-3-phenyl-propionic acid
2-[4'-(2-butyl-benzo[b]thiophene-3-yl)-biphenyl-4-yloxy]-3-phenyl-propionic acid
2-[4'-(2-benzyl-benzo[b]thiophene-3-yl)-biphenyl-4-yloxy]-3-phenyl-propionic acid
2-[4'-(2-benzoyl-benzofuran-3-yl)-biphenyl-4-yloxy]-3-phenyl-propionic acid
(2R)-2-[4'-(2-benzyl-benzofuran-3-yl)-biphenyl-4-yloxy]-3-phenyl-propionic acid
(2S)-2-[4'-(2-benzyl-benzofuran-3-yl)-biphenyl-4-yloxy]-3-phenyl-propionic acid
(2S )-2-[4'-(2-benzyl-benzofuran-3-yl)-biphenyl-4-yloxy]-3-phenyl-propionic acid tromethamine salt
(2R)-2-[4'-(2-benzyl-benzofuran-3-yl)-biphenyl-4-yloxy]-propionic acid
(R)-[4'-(2-benzyl-benzofuran-3-yl)-biphenyl-4-yloxy]-phenyl-acetic acid
(2R)-2-{4'-[2-(4-fluoro-benzyl-benzo[b]thiophene-3-yl)-biphenyl-4-yloxy]-3-phenyl-propionic acid
(2R)-2-{4'-[2-(4-methoxy-benzyl-benzo[b]thiophene-3-yl)-biphenyl-4-yloxy]-3-phenyl-propionic acid

[4'-(2-butyl-benzo[b]thiophene-3-yl)-biphenyl-4-yloxy]-phenyl-acetic acid (2R)-2-{4'-[2-(hydroxy-phenyl-methyl)-benzofuran-3-yl)-biphenyl-4-yloxy]-3-phenyl-propionic acid (2S)-2-[4'-(2-benzyl-benzofuran-3-yl)-biphenyl-4-yloxy]-3-phenyl-propionic acid methyl ester 2-[4'-(2-benzyl-benzofuran-3-yl)-biphenyl-4-yloxy]-2-methyl-3-phenyl-propionic acid (2R)-2-{4'-[2-(3,4-dimethoxy-benzyl)-benzo[b]thiophene-3-yl)-biphenyl-4-yloxy]-3-phenyl-propionic acid (2R)-2-{4'-[2-(2,4-dimethoxy-benzyl)-benzo[b]thiophene-3-yl)-biphenyl-4-yloxy]-3-phenyl-propionic acid (2R)-2-{4'-[2-(2,2-dimethyl-benzo[1,3]dioxol-5-ylmethyl)-benzo[b]thiophen-3-yl)-biphenyl-4-yloxy]-3-phenyl-propionic acid (2R)-2-{4'-[2-(3,4-dihydroxy-benzyl)-benzo[b]thiophene-3-yl)-biphenyl-4-yloxy]-3-phenyl-propionic acid (2R)-2-[4'-(2-benzyl-thiophene-3-yl)-biphenyl-4-yloxy]-3-phenyl-propionic acid 3-phenyl-2-[4'-(2-thiazole-2-ylmethyl-benzo[b]thiophene-3-yl)-biphenyl-4-yloxy]-propionic acid (2R)-3-phenyl-2-[4'-(2-pyridin-2-ylmethyl-benzo[b]thiophene-3-yl)-biphenyl-4-yloxy]-propionic acid sodium salt (2R)-3-phenyl-2-[4'-(2-pyridin-2-ylmethyl-benzo[b]thiophene-3-yl)-biphenyl-4-yloxy]-propionic acid (2S)-2-[4'-(2-benzyl-furo[2,3]pyridin-3-yl)-biphenyl-4-yloxy]-3-phenyl-propionic acid 4'-(2-benzyl-benzo[b]thiophene-3-yl)-3-bromo-biphenyl-4-ol 4'-(2-benzyl-benzo[b]thiophene-3-yl)-3,5-dibromo-biphenyl-4-ol (2R)-2-[4'-(2-benzyl-benzo[b]thiophene-3-yl)-3-bromo-biphenyl-4-yloxy]-3-phenyl-propionic acid (2R)-2-[4'-(2-benzyl-benzo[b]thiophene-3-yl)-3,5-dibromo-biphenyl-4-yloxy]-3-phenyl-propionic acid (2R)-2-[4-(2-benzyl-benzo[b]thiophene-3-yl)-4"-methoxy-[1,1';3',1"]terphenyl-4'-yloxy]-3-phenyl-propionic acid

[(4,4"-dimethoxy-5'-{2-(phenylmethyl)benzo[b]thien-3-yl]phenyl}[1,1';3',1"-terphenyl]-2'-yl)oxy]-acetic acid

[4-(2-benzyl-benzo[b]-thiophen-3-yl)-5'-bromo-4"-methoxy[1,1';3',1"-terphenyl]-4'-yl)oxy]-acetic acid

[4'-(2-benzyl-benzo[b]thiophene-3-yl)-3,5-dibromo-biphenyl-4-yloxy]-acetic acid

[4'-(2-benzyl-benzo[b]thiophene-3-yl)-3-bromo-biphenyl-4-yloxy]-acetic acid (2S)-[4'-(2-benzyl-benzo[b]thiophene-3-yl)-3,5-dibromo-biphenyl-4-yloxy]-4-phenyl-butyric acid 4-[4'-(2-benzyl-benzo[b]thiophene-3-yl)-3-bromo-biphenyl-4-yloxy]-butyric acid N-{(3R)-3-[4'-(2-benzyl-benzo[b]thiophen-3-yl)-3,5-dibromo-biphenyl-4-yloxy]-3-carboxy-propyl]-phthalamic acid N-{(3R)-3-[4'-(2-benzyl-benzo[b]thiophen-3-yl)-3,5-dibromo-biphenyl-4-yloxy]-3-methoxycarbonyl-propyl]-phthalamic acid (2R)-2-[4-(2-benzyl-benzo[b]thiophene-3-yl)-4"-chloro-[1,1';3',1"]terphenyl-4'-yloxy]-3-phenyl-propionic acid (2S)-2-[4'-(2-benzyl-benzofuran-3-yl)-biphenyl-4-yloxy]-4-phenyl-butyric acid (2R)-2-[4'-(2-benzyl-benzo[b]-thiophen-3-yl)-3,5-dibromo-biphenyl-4-yloxy]-4-(1,3-dioxo-1,3-dihydro-isoindol-2-yl)-butyric acid (2R)-2-[4'-(2-benzyl-benzofuran-3-yl)-biphenyl-4-yloxy]-4-(1,3-dioxo-1,3-dihydro-isoindol-2-yl)-butyric acid (2S)-2-[4'-(2-benzyl-benzofuran-3-yl)-3,5-dibromo-biphenyl-4-yloxy]-3-phenyl-propionic acid (2S)-2-[4'-(2-benzyl-benzofuran-3-yl)-3-bromo-biphenyl-4-yloxy]-3-phenyl-propionic acid (2R)-2-[4'-(2-benzyl-benzofuran-3-yl)-3,5-dibromo-biphenyl-4-yloxy]-4-methyl-pentanoic acid 2-[4'-(2-benzyl-benzofuran-3-yl)-3,5-dibromo-biphenyl-4-yloxy]-hexanoic acid (2S)-2-[4'-(2-benzyl-benzofuran-3-yl)-3,5-dibromo-biphenyl-4-yloxy]-butyric acid (2S)-2-[4'-(2-benzyl-benzofuran-3-yl)-3,5-dibromo-biphenyl-4-yloxy]-octanoic acid (2S)-2-[4-(2-benzyl-benzofuran-3-yl)-4"-methoxy-[1,1';3',1"]terphenyl-4'-yloxy]-3-phenyl-propionic acid

[4-(2-benzyl-benzo[b]-thiophen-3-yl)-5'-bromo-3",4"-dimethoxy[1,1';3',1"-terphenyl]-4'-yl)oxy]-acetic acid

[4-(2-benzyl-benzo[b]-thiophen-3-yl)-5'-bromo-3"-methoxy[1,1';3',1"-terphenyl]-4'-yl)oxy]-acetic acid

[[3,3-dimethoxy-5-[4-[2-(phenylmethyl)benzyl-benzo[b]-thiophen-3-yl)-[1,1';3',1"-terphenyl]-4'-yl)oxy]-acetic acid

[4-(2-benzyl-benzo[b]-thiophen-3-yl)-4"-methoxy[1,1';3',1"-terphenyl]-4'-yl)oxy]-acetic acid

[4-(2-benzyl-benzo[b]-thiophen-3-yl)-3",4"-dimethoxy[1,1';3',1"-terphenyl]-4'-yl)oxy]-acetic acid

[4-(2-benzyl-benzo[b]-thiophen-3-yl)-3",4",5"-trimethoxy[1,1';3',1"-terphenyl]-4'-yl)oxy]-acetic acid

[4-(2-benzyl-benzo[b]-thiophen-3-yl)-[1,1';3',1"-terphenyl]-4'-yl)oxy]-acetic acid 4-[4'-(2-benzyl-benzofuran-3-yl)-biphenyl-4-yloxymethyl]-benzoic acid (2S)-2-[4'-(1-benzyl-1H-benziridazol-2-yl)-biphenyl-4-yloxy]-3-phenyl-propionic acid (2R)-2-[4'-(3-benzyl-3H-imidazol[4,5-b]pyridin-2-yl)-biphenyl-4-yloxy]-3-phenyl-propionic acid sodium salt (2R)-2-[4'-(2-benzyl-4,5-dimethyl-thiophen-3-yl)-biphenyl-4-yloxy]-3-phenyl-propionic acid (2R)-2-[4'-(2-benzoyl-benzofuarn-3-yl)-3-nitro-biphenyl-4-yloxy]-3-phenyl-propionic acid (2R)-2-[4'-(2-benzyl-benzofuarn-3-yl)-3-nitro-biphenyl-4-yloxy]-3-phenyl-propionic acid (2R)-2-[4'-(2-(hydroxy-phenyl-methyl)-benzofuarn-3-yl)-3-nitro-biphenyl-4-yloxy]-3-phenyl-propionic acid (2S)-2-[4'-(2-benzyl-benzofuarn-3-yl)-3,5-dimethyl-biphenyl-4-yloxy]-3-phenyl-propionic acid (2S)-2-[4'-(5-acetyl-thiophen-2-yl)-biphenyl-4-yloxy]-3-phenyl-propionic acid sodium salt or a pharmaceutically acceptable salt thereof.

The compounds of this invention were prepared according to the following schemes from commercially available starting materials or starting materials which can be prepared using literature procedures. These schemes show the preparation of representative compounds of this invention.

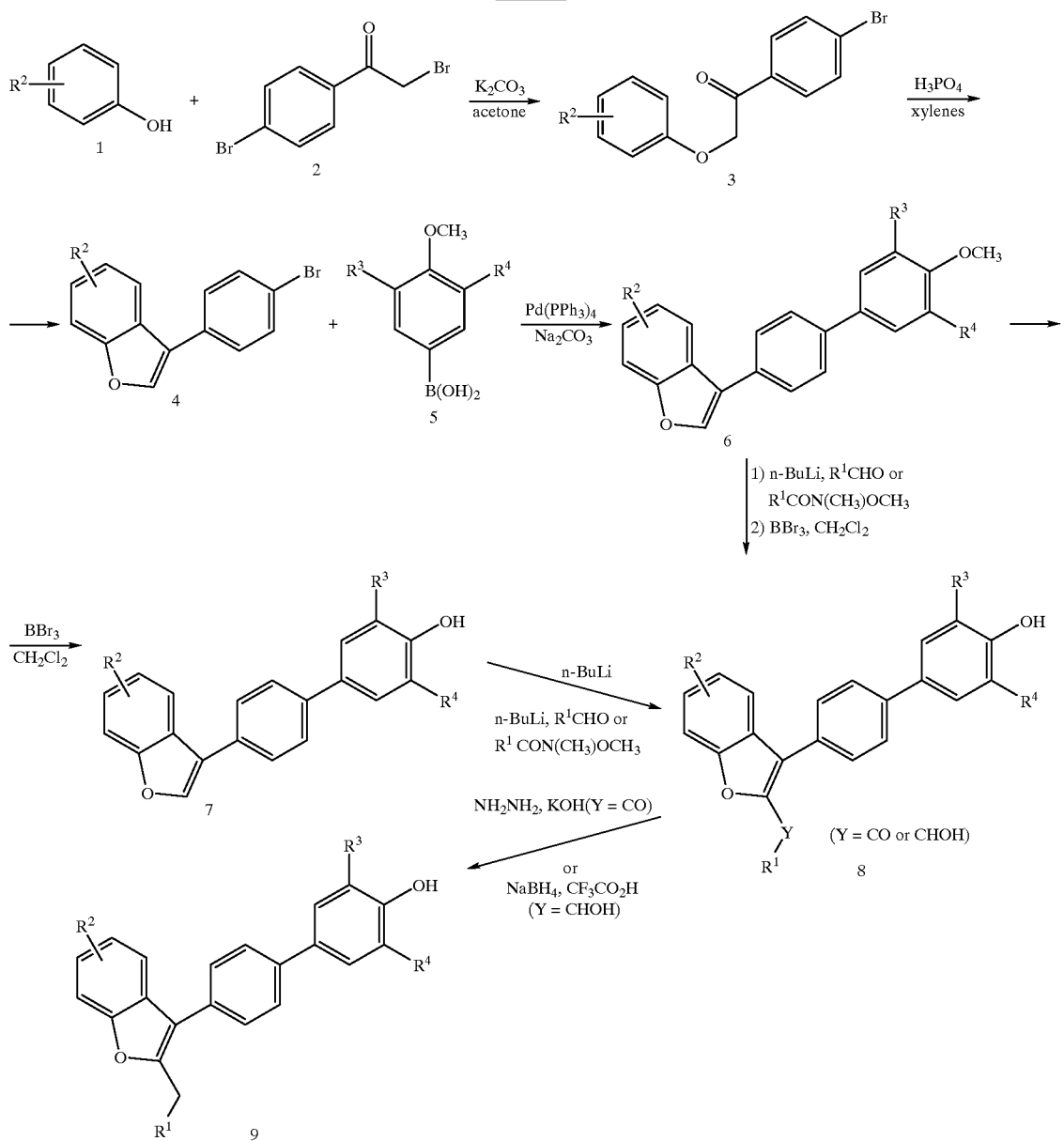

Scheme I

In Scheme I, commercially available phenols (1; $R^2$ as defined above) were treated with 4-bromophenylacyl bromide (2) in the presence of potassium carbonate to produce ketones (3). Compounds (3) were treated with polyphosphoric acid at high temperatures (150° C.) to afford benzofurans (4) [ref. J. Med. Chem. 1989, 32, 1700–1707]. Benzofurans (4) were coupled with aryl boronic acids of general structure (5; $R^3$, $R^4$ are alkyl, aryl, trifluoromethyl, substituted aryl, nitro, carbocyclic 5 to 7 carbon atoms rings or heterocyclic rings 5 to 7 atom rings with from 1 to 3 heteroatoms selected from oxygen, nitrogen, and sulfur) using the Suzuki protocol [ref. Syn. Comm. 1981, 11, 513–519] to produce biphenyls (6). The aryl boronic acids are either commercially available or can be prepared according to known methodology [ref. J. Org. Chem, 1984, 49, 5237–5243]. Biphenyls (6) were converted to biphenyls (8) using two different synthetic approaches. In the first synthetic approach, biphenyls (6) were treated first with n-BuLi and either aldehydes $R^1$CHO or "Weinreb" amides $R^1$CON(CH$_3$)OCH$_3$ ($R^1$ is as defined above with the exception of halogen), and secondly with boron tribromide in dichloromethane to produce biphenyls (8). In the second synthetic approach, biphneyls (6) first converted to biphenyls (7) with boron tribromide in dichloromethane [ref. J. Org. Chem. 1974, 39, 1427–1429], and then biphenyls (7) were converted to biphenyls (8) by using n-BuLi and either aldehydes $R^1$CHO or "Weinreb" amides $R^1$CON(CH$_3$)OCH$_3$. The required aldehydes and "Weinreb" amides are either commercially available or can be prepared according to known synthetic methodology [ref. Tet. Lett. 1993, 34, 6215–6218]. Biphenyls (8) were converted to biphenyls (9) by reduction of the ketones (Y=CO) using the Wolff-Kishner reduction (NH$_2$NH$_2$, KOH; ref. Org. Reactions, 1948, 4, 378), or reduction of the secondary hydroxy group (Y=CHOH) with sodium borohydride in trifluoroacetic acid [ref. Syn. Comm. 1990, 20, 487–493].

Scheme II

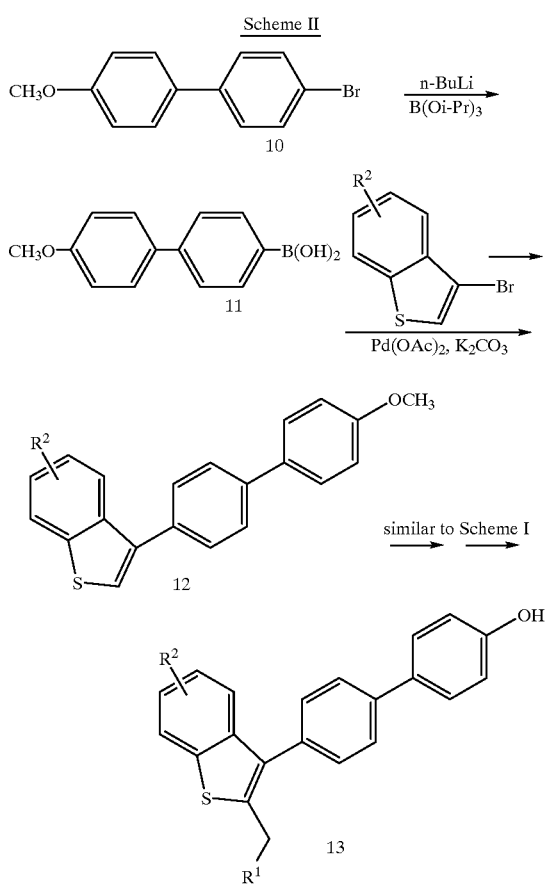

In Scheme II, the biphenyl boronic acid (11) was prepared from 10 according to known methodology [ref. J. Org. Chem. 1984, 49, 5237–5243] using n-BuLi to generate the aryllithium intermediate which was subsequently treated with triisopropyl borate. Boronic acid (11) was coupled with 3-bromobenzothiophenes (prepared according to reference J. Am. Chem. Soc. 1950, 72, 571–574) using the Suzuki protocol [ref. Syn. Comm. 1981, 11, 513–519] to produce biphenyls (12). Biphenyls (12) were converted to the biphenyls (13) in a similar manner as described in Scheme I for the conversion of biphenyls (6) to biphenyls (9).

Scheme III

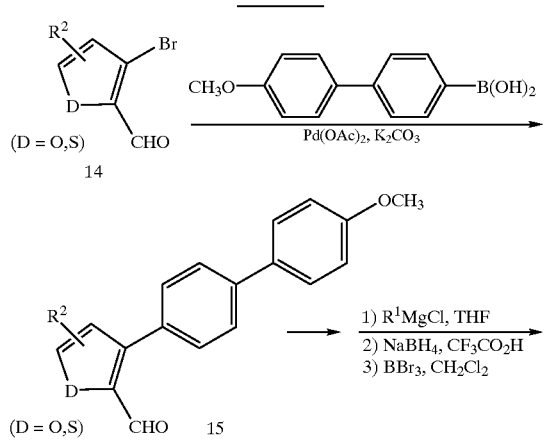

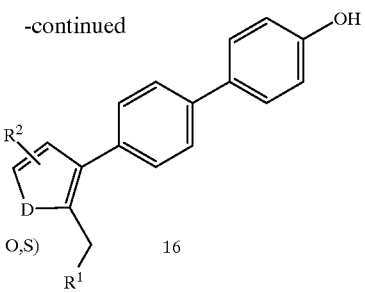

In Scheme III, thienyl and furyl aldehydes (14) are either commercially available or can be prepared from substituted furans or thiophenes. Furans or thiophenes undergo metallation at the 2-position with alkyllithium reagents [J. Chem. Soc. Perkin I, 1977, 887] which upon treatment first with a formulating agent (i.e., dimethylformamide), and secondly bromination according to known methodology [ref. J. Am. Chem. Soc. 1950, 72, 571–574] to afford the required compounds (14). Coupling of aldehydes (14) with 4,4'-methoxy biphenyl boronic acid using the Suzuki protocol [ref. Syn. Comm. 1981, 11, 513–519] gave biphenyls (15). Known or easily prepared Grignard Reagents [ref. Chem. Re. 1954, 54, 835] $R^1$Mg(Cl or Br) ($R^1$ is as defined above with the exception of halogen, trifluoromethyl, lower alkoxy) were first treated with aldehydes (14), followed by reduction of the produced methyl-hydroxy compounds with sodium borohydride and trifluoroacetic acid, and then demethylation with boron tribromide in dichoromethane to afford biphenyls (16).

Scheme IV

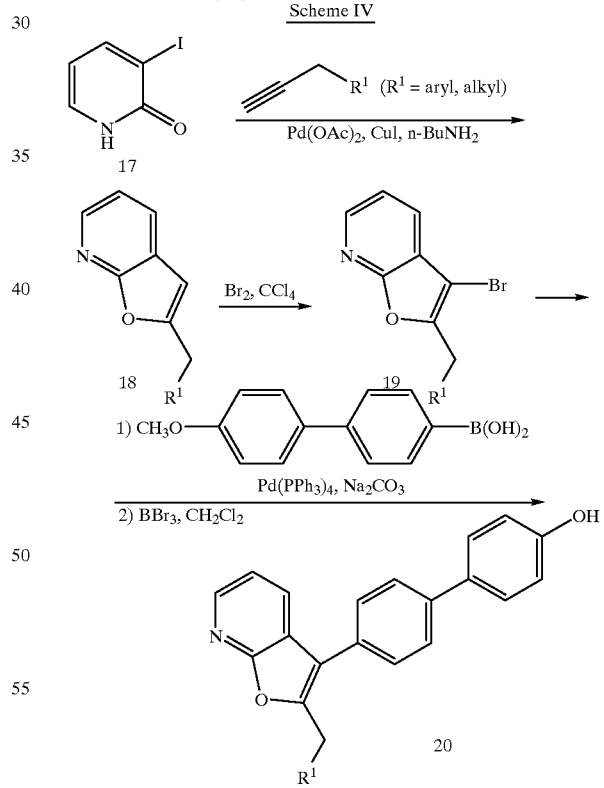

In Scheme IV, the furo[2,3-b]pyrinines (18) ($R^1$ is aryl or alkyl) were prepared according to known methodology [ref. Tet. Lett. 1994, 35, 9355–9358]. Bromination of 18 with $Br_2$ in carbon tetrachloride produced 19. Pyridines (19) were converted to biphenyls (20) in a similar manner as described in Scheme I by Suzuki coupling with 4, 4'-methoxy biphenyl boronic acid, and demethylation with boron tribromide.

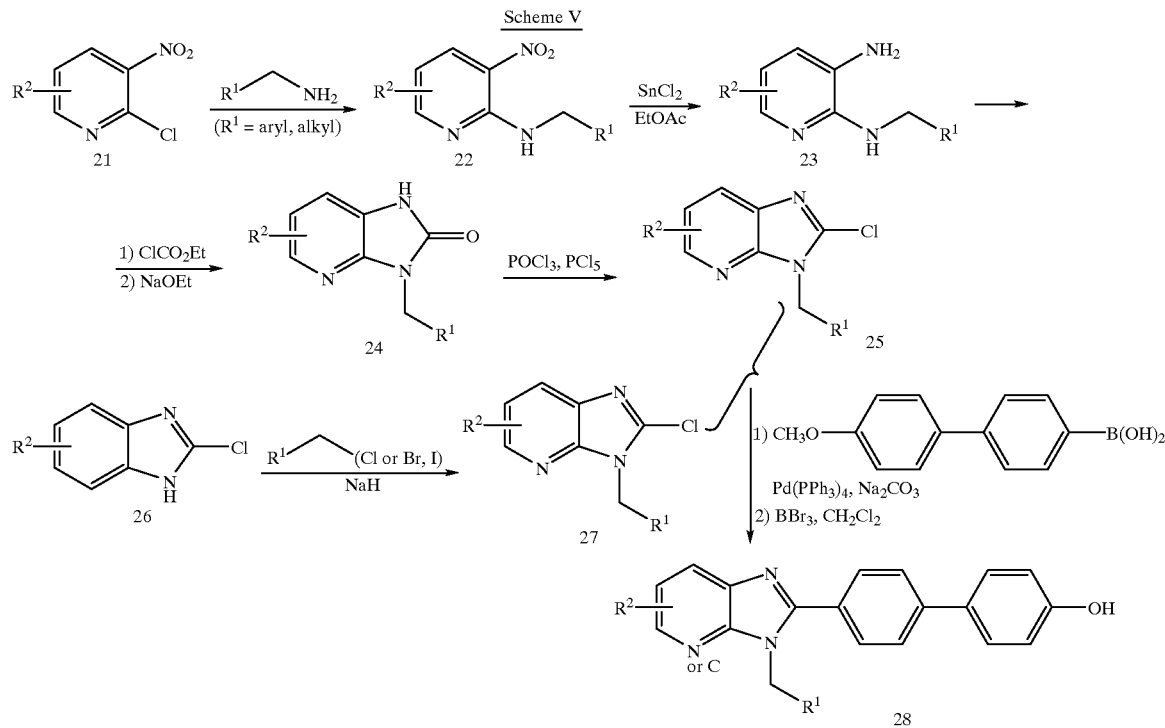

In Scheme V, the chloro-nitro-pyridines (21) were treated with primary amines to produce nitro-pyridines (22). The nitro-pyridines (22) were reduced with tin chloride to anilines (23), which upon treatment with ethyl chloroformate and sodium ethoxide gave imidazolones (24). The imidazolones (24) were converted to the 2-chloro-imidazole[4,5-b]pyridines (25). 2-Chlorobenzimidazoles (26) were alkylated in the presence of sodium hydride to give benzimidazoles (27). Both, the imidazole[4,5-b]pyridines (25), and benzimidazoles (27) were converted to the biphenyls (28) in a similar manner as described in Scheme 1 by Suzuki coupling with 4, 4'-methoxy biphenyl boronic acid, and demethylation with boron tribromide.

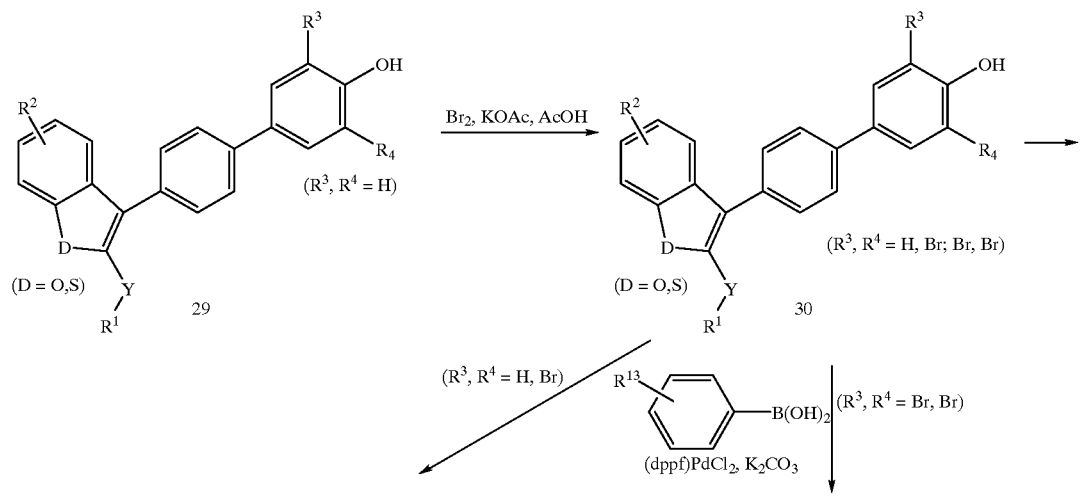

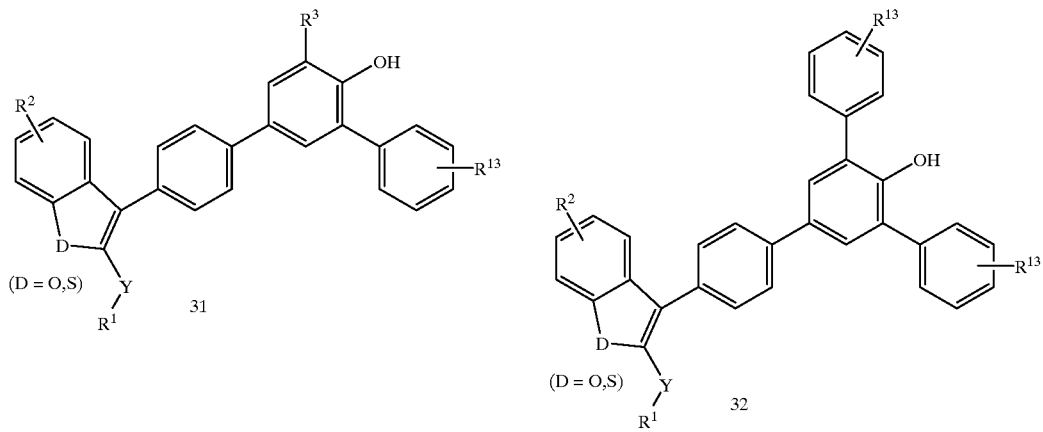

In Scheme VI, the biphenyl compounds (29; Y=CO, CH$_2$) can be monobrominated or dibrominated using bromine, potassium acetate and acetic acid. One equivalent of bromine in a high dilution reaction mixture and low temperatures in the range of 5–10° C. afforded predominantly the monobrominated product (30; R$^3$, R$^4$=H, Br). The dibrominated product (30; R$^3$, R$^4$=Br, Br) was obtained with two equivalents of bromine at room temperature. The Suzuki coupling protocol [ref. Syn. Comm. 1981, 11, 513–519] was used to generate the terphenyls 31 and 32. Coupling of the monobromo compounds (30; R$^3$, R$^4$=H, Br) with boronic acids R$^{13}$—Ar—B(OH)$_2$; (R$^{13}$=halogen, trifluoromethyl, alkoxy, alkyl, nitro, amino, carboalkoxy) in the present of an inorganic base, for example K$_2$CO$_3$, Ba(OH)$_2$, and palladium (0 or II) catalyst, for example Pd(PPh$_3$)$_4$, Pd(OAc)$_2$, (dppf)PdCl$_2$, produced terphenyls (31; R$^3$=H). Similarly, the dibromo compounds (30; R$^3$, R$^4$=Br, Br) can undergo Suzuki coupling to afford either the di-coupled product (32) by using 2 equivalents of boronic acid at high temperatures (100° C.), or the mono-coupled-mono-bromo product (31; R$^3$, R$^4$=Br, Aryl-R$^{13}$). Both the bromo and dibromo compounds can afford in the same synthetic manner products with various heterocyclic boronic acids, for example thiophene, furan, oxazole, thiazole, pyridine).

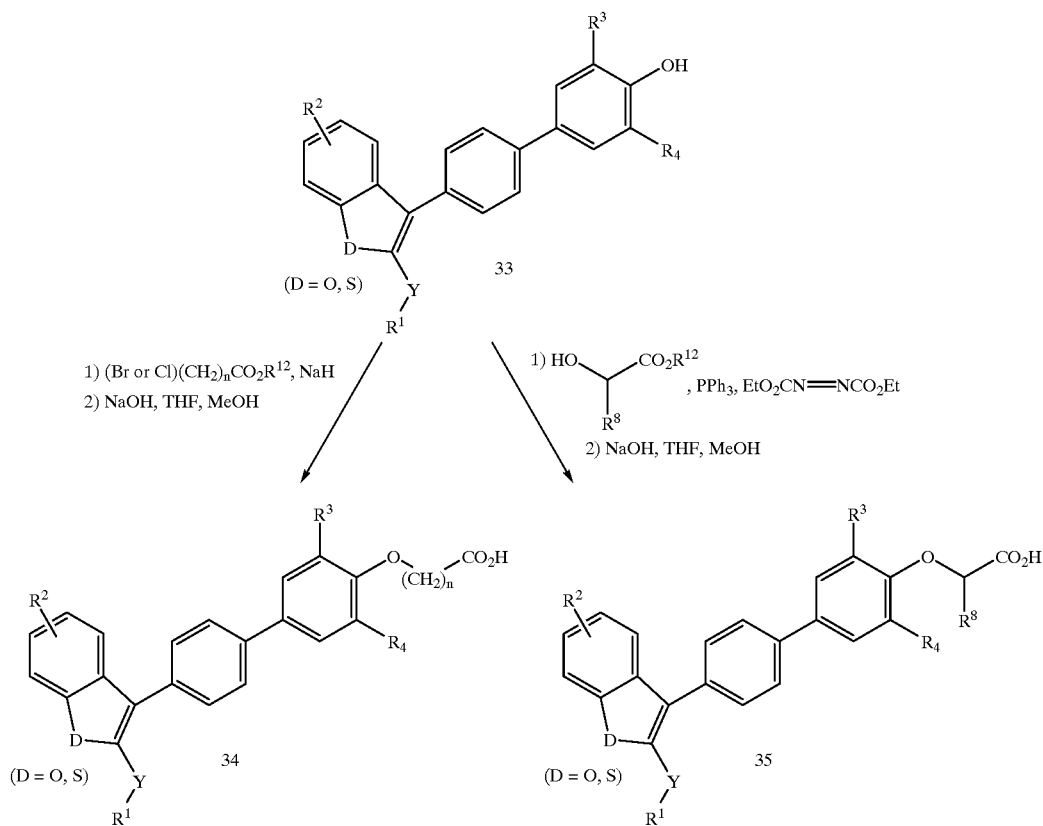

In Scheme VII, the biphenyls (33) were alkylated with bromo or chloro-alkylcarboxylates [(Br or Cl)(CH$_2$)$_n$CO$_2$R$^{12}$] in the presence of sodium hydride or potassium carbonate, using dimethylformamide or acetonitrile as the solvent. Subsequent saponification with sodium hydroxide in methyl alcohol and tetrahydrofuran produced biphenyls (34). Coupling of biphenyls (33) with hydroxy-alkyl-carboxylates [HOCH(R$^8$)CO$_2$R$^{12}$] using the Mitsunobu protocol [ref. *Synthesis*. 1981, 1–27], followed by saponification with sodium hydroxide in methyl alcohol and tetrahydrofuran produced biphenyls (35). Similar experimental protocols were applied and for the biphenyls 16, 20, 28 and 32, for the production of compounds of Formula I.

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was established with representative compounds of this invention in the following two standard pharmacological test procedures which measure the inhibition of PTPase.

Inhibition of Tri-phosphorylated Insulin Receptor Dodecaphosphopeptide Dephoslphoylation by Rat Hepatic Protein-tyrosine Phosphatases (PTPases)

This standard pharmacological test procedure assess the inhibition of rat hepatic microsomal PTPase activity using, as substrate, the phosphotyrosyl dodecapeptide corresponding to the 1142–1153 insulin receptor kinase domain, phosphorylated on the 1146, 1150 and 1151 tyrosine residues. The procedure used an d results obtained are briefly outlined below.

Preparation of Microsomal Fraction:

Rats (Male Sprague-Dawley rats (Charles River, Kingston, N.Y.) weighing 100–150 g, maintained on standard rodent chow (Purina)) are sacrificed by asphyxiation with CO2 and bilateral thoracotomy. The liver is removed and washed in cold 0.85% (w/v) saline and weighed. The tissue is homogenized on ice in 10 volumes of Buffer A and the microsomes are isolated essentially as described by Meyerovitch J, Rothenberg, P, Shechter Y, Bonner-Weir S, Kahn C R. Vanadate normalizes hyperglycemia in two mouse models of non-insulin-dependent diabetes mellitus. *J Clin Invest* 1991; 87:1286–1294 and Alberts B, Bray D, Lewis J, Raff M, Roberts K, Watson JD, editors. Molecular biology of the cell. New York: Garland Publishing, Inc., 1989 with minor modifications. The liver homogenate is filtered through silk to remove any remaining tissue debris and then is centrifuged at 10,000×g for 20 minutes at 40C. The supenatant is decanted and centrifuged at 100,000×g for 60 minutes at 40C. The pellet, microsomes and small vesicles, is resuspended and lightly homogenized in: 20 rM TRIS-HCl (pH 7.4), 50 mM 2-mercaptoethanol, 250 mM sucrose, 2 mM EDTA, 10 mM EGTA, 2 mM AEBSF, 0.1 mM TLCK, 0.1 mM TPCK, 0.5 mM benzamidine, 25 ug/ml leupeptin, 5 ug/ml pepstatin A, 5 ug/ml;H5B antipain, 5 ug/ml chymostatin, 10 ug/ml aprotinin (Buffer A), to a final concentration of approximately 850 ug protein/ml. Protein concentration is determined by the Pierce Coomassie Plus Protein Assay using crystalline bovine serum albumin as a standard (Pierce Chemical Co., Rockford, Ill).

Measurement of PTPase Activity:

The malachite green-ammonium molybdate method, as described by Lanzetta P A, Alvarez L J, Reinach P S, Candia O A was used. An improved assay for nanomolar amounts of inorganic phosphate. *Anal. Biochem*. 1979;100:95–97, and adapted for the platereader, is used for the nanomolar detection of liberated phosphate by rat hepatic microsomal PTPases. The test procedure uses, as substrate, a dodecaphosphopeptide custom synthesized by AnaSpec, Inc. (San Jose, Calif.). The peptide, TRDIYETDYYRK, corresponding to the 1142–1153 catalytic domain of the insulin receptor, is tyrosine phosphorylated on the 1146, 1150 and 1151 tyrosine residues. The microsomal fraction (83.25 ul) is preincubated for 10 min at 37 deg.C. with or without test compound (6.25 ul) and 305.5 ul of the 81.83 mM HEPES reaction buffer, pH 7.4. Peptide substrate, 10.5 ul at a final concentration of 50 uM, is equilibrated to 37 deg.C. in a LABLINE Multi-Blok heater equipped with a titerplate adapter. The preincubated microsomal preparation (39.5 ul) with or without drug is added to initiate the dephosphorylation reaction, which proceeds at 37 deg.C. for 30 min. The reaction is terminated by the addition of 200 ul of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 ul MG/AM/Tw to substrate and followed by 39.5 ul of the preincubated membrane with or without drug. The color is allowed to develop at room temperature for 30 min and the sample absorbances are determined at 650 nm using a platereader (Molecular Devices). Samples and blanks are prepared in quadruplicates. Screening activity of 50 uM (final) drug is accessed for inhibition of microsomal PTPases.

Calculations:

PTPase activities, based on a potassium phosphate standard curve, are expressed as nmoles of phosphate released/min/mg protein. Test compound PTPase inhibition is calculated as percent of control. A four parameter non-linear logistic regression of PTPase activities using SAS release 6.08, PROC NLIN, is used for determining IC50 values of test compounds. All compounds were administered at a concentration of 50 $\mu$M. The following results were obtained using representative compounds of this invention.

| Example | % Change from Control |
|---|---|
| 1 | −53 |
| 2 | IC$_{50}$ = 28.4 uM |
| 3 | IC$_{50}$ = 29.9 uM |
| 4 | −11 |
| 5 | −70 |
| 6 | −71 |
| 7 | −73 |
| 8 | −28 |
| 9 | −75 |
| 10 | −72 |
| 11 | −61 |
| 12 | −50 |
| 13 | −50 |
| 14 | −55 |
| 15 | −59 |
| 16 | −53 |
| 17 | −63 |
| 18 | IC$_{50}$ = 24.2 uM |
| 19 | IC$_{50}$ = 21.4 uM |

-continued

| Example | % Change from Control |
|---|---|
| 20 | $IC_{50}$ = 41.6 uM |
| 21 | $IC_{50}$ = 35.5 uM |
| 22 | −55 |
| 25 | $IC_{50}$ = 17.9 uM |
| 26 | $IC_{50}$ = 20.0 uM |
| 27 | $IC_{50}$ = 24.9 uM |
| 28 | $IC_{50}$ = 20.6 uM |
| 29 | −19 |
| 36 | $IC_{50}$ = 17.9 uM |
| 37 | $IC_{50}$ = 36.8 uM |
| 38 | $IC_{50}$ = 19.3 uM |
| phenylarsine (Reference) | −57 |

Inhibition of Tri-Phosphorylated Insulin Receptor Dodecaphosphopeptide Dephosphorylation by hPTP1B This standard pharmacological test procedure assess the inhibition of recombinant rat protein tyrosine phosphatase, PTP1B, activity using, as substrate, the phosphotyrosyl dodecapeptide corresponding to the 1142–1153 insulin receptor kinase domain, phosphorylated on the 1146, 1150 and 1151 tyrosine residues. The procedure used and results obtained are briefly described below.

Human recombinant PTP1B was prepared as described by Goldstein (see Goldstein et al. *Mol. Cell. Biochem.* 109, 107, 1992). The enzyme preparation used was in microtubes containing 500–700 μg/ml protein in 33 mM Tris-HCl, 2 mM EDTA, 10% glycerol and 10 mM 2-mercaptoethanol. Measurement of PTPase Activity.

The malachite green-ammonium molybdate method, as described (Lanzetta et al. *Anal. Biochem.* 100, 95, 1979) and adapted for a platereader, is used for the nanomolar detection of liberated phosphate by recombinant PTP1B. The test procedure uses, as substrate, a dodecaphosphopeptide custom synthesized by AnaSpec, Inc. (San Jose, Calif.). the peptide, TRDIYETDYYRK, corresponding to the 1142–1153 catalytic domain of the insulin receptor, is tyrosine phosphorylated on the 1146, 1150, and 1151 tyrosine residues. The recombinant rPTP1B is diluted with buffer (pH 7.4, containing 33 mM Tris-HCl, 2 mM EDTA and 50 mM b-mercaptoethanol) to obtain an approximate activity of 1000–2000 nmoles/min/mg protein. The diluted enzyme (83.25 mL) is preincubated for 10 min at 37° C. with or without test compound (6.25 mL) and 305.5 mL of the 81.83 mM HEPES reaction buffer, pH 7.4 peptide substrate, 10.5 ml at a final concentration of 50 mM, and is equilibrated to 37° C. in a LABLINE Multi-Blok heater equipped with a titerplate adapter. The preincubated recombinant enzyme preparation (39.5 ml) with or without drug is added to initiate the dephosphorylation reaction, which proceeds at 37° C. for 30 min. The reaction is terminated by the addition of 200 mL of the malachite green-ammonium molybdate-Tween 20 stopping reagent (MG/AM/Tw). The stopping reagent consists of 3 parts 0.45% malachite green hydrochloride, 1 part 4.2% ammonium molybdate tetrahydrate in 4 N HCl and 0.5% Tween 20. Sample blanks are prepared by the addition of 200 mL MG/AM/Tw to substrate and followed by 39.5 ml of the preincubated recombinant enzyme with or without drug. The color is allowed to develop at room temperature for 30 min. and the sample absorbances are determined at 650 nm using a platereader (Molecular Devices). Sample and blanks are prepared in Calculation:

PTPase activities, based on a potassium phosphate standard curve, are expressed as nmoles of phosphate released/min/mg protein. Inhibition of recombinant PTP1B by test compounds is calculated as percent of phosphatase control. A four parameter non-liner logistic regression of PTPase activities using SAS release 6.08, PROC NLIN, is used for determining $IC_{50}$ values of test compounds. The following results were obtained.

| Example | IC50 (uM) |
|---|---|
| 1 | 0.322 |
| 2 | 0.025 |
| 3 | 0.029 |
| 4 | −51 (2.5 uM) |
| 5 | −47 (2.5 uM) |
| 6 | −15 (2.5 uM) |
| 7 | −58 (2.5 uM) |
| 8 | 0.74 |
| 9 | 2.19 |
| 10 | 0.44 |
| 11 | 0.27 |
| 12 | 0.176 |
| 13 | 0.095 |
| 14 | 0.68 |
| 15 | 0.348 |
| 16 | 0.397 |
| 17 | 1.32 |
| 18 | 0.401 |
| 19 | 0.123 |
| 20 | 0.077 |
| 21 | 0.118 |
| 22 | 0.118 |
| 23 | −36 (2.5 uM) |
| 24 | 0.293 |
| 25 | 0.213 |
| 26 | 0.085 |
| 27 | 0.077 |
| 28 | 0.122 |
| 29 | 0.97 |
| 30 | 1.16 |
| 31 | 0.59 |
| 32 | 1.51 |
| 33 | 1.55 |
| 34 | 1.07 |
| 35 | 0.454 |
| 36 | 0.058 |
| 37 | 0.025 |
| 38 | 0.053 |
| 39 | 0.105 |
| 40 | 0.362 |
| 41 | 0.29 |
| 42 | 0.178 |
| 43 | 0.044 |
| 44 | 0.054 |
| 45 | 0.181 |
| 46 | 0.052 |
| 47 | 0.225 |
| 48 | 0.341 |
| 49 | 0.038 |
| 50 | 0.056 |
| 51 | 0.054 |
| 52 | 0.052 |
| 53 | 0.133 |
| 54 | 0.023 |
| 55 | 0.043 |
| 56 | 0.047 |
| 57 | 0.028 |
| 58 | 0.025 |
| 59 | 0.08 |
| 60 | 0.071 |
| 61 | 0.100 |
| 62 | 0.105 |
| 63 | 0.369 |
| 64 | 0.512 |
| 65 | 0.074 |
| 66 | 0.788 |
| 67 | 0.103 |

-continued

| Example | IC50 (uM) |
|---|---|
| 68 | 0.231 |
| 69 | −20 (1 uM) |
| 70 | −41 (2.5 uM) |
| 71 | −43 (2.5 uM) |
| Phenylarsine oxide (reference standard) | 39.7 |
| Sodium orthovanadate (reference standard) | 244.8 |
| Ammonium molybdate tetrahydrate (reference standard) | 8.7 |

The blood glucose lowering activity of representative compounds of this invention were demonstrated in an in vivo standard procedure using diabetic (ob/ob) mice. The procedures used and results obtained are briefly described below.

The non-insulin dependent diabetic (NIDDM) syndrome can be typically characterizes by obesity, hyperglycemia, abnormal insulin secretion, hyperinsulinemia and insulin resistance. The genetically obese-hyperglycemic ob/ob mouse exhibits many of these metabolic abnormalities and is thought to be a useful model to search for hypoglycemic agents to treat NIDDM [Coleman, D.: Diabetologia 14: 141–148, 1978].

In each test procedure, mice [Male or female ob/ob (C57 B1/6J) and their lean litermates (ob/+ or +/+, Jackson Laboratories) ages 2 to 5 months (10 to 65 g)] of a similar age were randomized according to body weight into 4 groups of 10 mice. The mice were housed 5 per cage and are maintained on normal rodent chow with water ad libitum. Mice received test compound daily by gavage (suspended in 0.5 ml of 0.5% methyl cellulose); dissolved in the drinking water; or admixed in the diet. The dose of compounds given ranges from 2.5 to 200 mg/kg body weight/day. The dose is calculated based on the fed weekly body weight and is expressed as active moiety. The positive control, ciglitazone (5-(4-(1-methylcyclohexylmethoxy)benzyl)-2,4-dione, see Chang, A., Wyse, B., Gilchrist, B., Peterson, T. and Diani, A. Diabetes 32: 830–838, 1983.) was given at a dose of 100 mg/kg/day, which produces a significant lowering in plasma glucose. Control mice received vehicle only.

On the morning of Day 4, 7 or 14 two drops of blood (approximetly 50 ul) were collected into sodium fluoride containing tubes either from the tail vein or after decapitation. For those studies in which the compound was administered daily by gavage the blood samples were collected two hours after compound administration. The plasma was isolated by centrifugation and the concentration of glucose is measured enzymatically on an Abbott V.P. Analyzer.

For each mouse, the percentage change in plasma glucose on Day 4, 7 or 14 is calculated relative to the mean plasma glucose of the vehicle treated mice. Analysis of variance followed by Dunett's Comparison Test (one-tailed) are used to estimate the significant difference between the plasma glucose values from the control group and the individual compound treated groups (CMS SAS Release 5.18).

The results shown in the table below shows that the compounds of this invention are antihyperglycemic agents as they lower blood glucose levels in diabetic mice.

| Example | Dose (mg/Kg) | % Change Glucose from Vehicle | % Change Insulin from Vehicle |
|---|---|---|---|
| 1 | 100 | −40.3 | 17a |
| 2 | 25 | −25.5 | 11.2a |
| 3 | 25 | −29.9 | 23.5a |
| 10 | 100 | −34.2 | −51.9 |
| 11 | 100 | −40.4 | −44.9 |
| 12 | 100 | −27.5 | −15.8a |
| 13 | 100 | −36.7 | 5.0a |
| 14 | 100 | −39 | 19.8a |
| 15 | 100 | −35 | 4.1a |
| 17 | 100 | 13.7a | −94.4 |
| 19 | 100 | −27.7 | 1.1a |
| 24 | 25 | −30.5 | not determined |
| 28 | 25 | −20 | not determined |
| 42 | 25 | −10.6 | 9.9a |
| 48 | 25 | 4.7a | −30 |
| 55 | 25 | −13.6 | 35.4a |
| Ciglitazone (reference standard | 100 | −43 | −39 | a-no significant activity (p < 0.05) at this dose.

Based on the results obtained in the standard pharmacological test procedures, representative compounds of this invention have been shown to inhibit PTPase activity and lower blood glucose levels in diabetic mice, and are therefore useful in treating metabolic disorders related to insulin resistance or hyperglycemia, typically associated with obesity or glucose intolerance. More particularly, the compounds of this invention useful in the treatment or inhibition of type II diabetes, and in modulating glucose levels in disorders such as type I diabetes. As used herein, the term modulating means maintaining glucose levels within clinically normal ranges.

Effective administration of these compounds may be given at a daily dosage of from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s). Suppository formulations may be made from traditional materials, including cocoa butter, with or without the addition of waxes to alter the suppository's melting point, and glycerin. Water soluble suppository bases, such as polyethylene glycols of various molecular weights, may also be used.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The following procedures describe the preparation of representative examples of this invention.

EXAMPLE 1

(2S)-2-[4'-(2-Benzyl-benzofuran-3-yl)-biphenyl-4-yloxy]-3-phenyl-propionic acid

Step a) ω-Phenoxy-4-bromoacetophenone

Potassium carbonate (24.8 g, 179.8 mmol) was added into a mixture of 4-bromophenylacyl bromide (50.0 g, 179.8 mmol), phenol (16.9 g, 179.8 mmol) and dry acetone (200 mL). The reaction mixture was refluxed for 12 hours, cooled to room temperature, poured into water, and extracted with ethyl ether. The organic extracts were dried over $MgSO_4$. Evaporation gave a yellow solid (49.6 g, 94% yield): MS m/e 291 ($M^+$).

Step b) 3-(4-Bromophenyl)-1-benzofuran

A mixture of ω-phenoxy-4-bromoacetophenone (49.0 g, 167.8 mmol), polyphosphoric acid (100 g) and xylenes (300 mL) was refluxed for 12 hours. The reaction mixture cooled to room temperature, poured into water, and extracted with ethyl ether. The organic extracts were dried over $MgSO_4$. Evaporation and purification by flash chromatography on silica gel (hexanes/EtAOc 40:1) gave a yellow solid (36.2 g, 79% yield): mp 70–71° C.; MS m/e 272 ($M^+$);

Analysis for: $C_{14}H_9BrO$ Calc'd: C, 61.57; H, 3.32; Found: C, 61.80; H, 3.31

Step c) 3-(4'-Methoxy-biphenyl-4-yl)-benzofuran

4-Methoxy-benzeneboronic acid (14.17 g, 70.5 mmol) in ethyl alcohol (10 mL) was added into a mixture of 3-(4-bromophenyl)-1-benzofuran (17.5 g, 64.1 mmol), sodium carbonate (2N, 64.1 mL), tetrakis(triphenylphosphine)palladium(0) (2.23 g, 1.92 mmol), and toluene (200 mL). The reaction mixture was refluxed for 12 hours, cooled to room temperature, and treated with hydrogen peroxide (30%, 5 mL) for 1 hour. Then, the mixture was poured into water and extracted with ethyl acetate. The organic extracts were dried over $MgSO_4$. Evaporation and crystallization from acetone/ethyl ether gave a white solid (14.9 g, 77% yield): mp 137–138° C.; MS m/e 300 ($M_+$);

Analysis for: $C_{21}H_{16}O_2$ Calc'd: C, 83.98; H, 5.37 Found: C, 83.70; H, 5.22

Step d) 4'-Benzofuran-3-yl-biphenyl-4-ol

Boron tribromide (1.0 M, 6.67 mL, 6.67 mmol) was added dropwise into a cold (−78° C.) mixture of 3-(4'-methoxy-biphenyl-4-yl)-benzofuran (2.0 g, 6.67 mmol), and dichloromethane (25 mL). The reaction mixture was allowed to come gradually to room temperature and stirred for 10 hours. Then the mixture cooled to 0° C. and methyl alcohol (5 mL) was added dropwise. After stirring for 10 minutes the mixture was poured into water and extracted with ethyl ether. The organic extracts were dried over $MgSO_4$. Evaporation and crystallization from ethyl ether/hexanes gave a yellow solid (1.69 g, 87% yield): mp 174–175; MS m/e 286 ($M^+$);

Analysis for: $C_{20}H_{14}O_2$ Calc'd: C, 83.90; H, 4.93 Found: C, 83.69; H, 4.88

Step e) [3-(4'-Hydroxy-biphenyl-4-yl)-benzofuran-2-yl]-phenyl-methanone n-Butyllithium (2.5 N, 8.4 mL, 20.98 mmol) was added dropwise into a cold (−78° C.) mixture of 4'-benzofuran-3-yl-biphenyl-4-ol (3.0 g, 10.49 mmol) and tetrahydrofuran (50 mL). The mixture was allowed to gradually warm up to −40° C. and stirred for 3 hours. N-Methoxy N-methyl benzamide (1.6 mL, 10.49 mmol) was added dropwise into the mixture. The reaction mixture was allowed to gradually warm up to 0° C. and stirred for 30 minutes. The reaction was quenched with aqueous ammonium chloride, poured into water, acidified with HCl (2N), and extracted with ethyl acetate. The organic extracts were dried over $MgSO_4$. Evaporation and crystallization from ethyl ether/hexanes gave a yellow solid (2.9 g, 71% yield): mp 231–232; MS m/e 390 ($M^+$);

Analysis for: $C_{27}H_{18}O_3$ Calc'd: C, 83.06; H, 4.65 Found: C, 82.63; H, 4.27

Step f) 4'-(2-Benzyl-benzofuran-3-yl)-biphenyl-4-ol

Hydrazine monohydrate (1.38 g, 27.68 mmol) was added into a mixture of [3-(4'-hydroxy-biphenyl-4-yl)-benzofuran-2-yl]-phenyl-methanone (2.7 g, 6.92 mmol) and diethylene glycol (20 mL). The reaction mixture was stirred at 180° C. for 1 hour. The mixture cooled to room temperature and potassium hydroxide (1.16 g, 20.76 mmol) was gradually added. The mixture stirred at 130° C. for 10 hours, cooled to room temperature , poured into water, and extracted with ethyl ether. The organic extracts were dried over $MgSO_4$. Evaporation and crystallization from ethyl ether/hexanes/acetone gave a white solid (2.45 g, 94% yield): mp 151–153; MS m/e 376 ($M^+$);

Analysis for: $C_{27}H_{20}O_2$ Calc'd: C, 86.15; H, 5.36 Found: C, 85.88; H, 5.13

Step g) (2S)-2-[4'-(2-Benzyl-benzofuran-3-yl)-biphenyl-4-yloxy]-3-phenyl-propionic acid methyl ester Diethylazodicarboxylate (1.67 mL, 10.64 mmol) in benzene (20 mL) was added dropwise into a cold (0° C.) mixture of 4'-(2-benzyl-bnzofuran-3-yl)-biphenyl-4-ol (2.0 g, 5.32 mmol), (R)-(+)-3-phenyllactic acid methyl ester (1.91 g, 10.64 mmol), triphenylphosphine (2.8 g, 10.64 mmol) and benzene (50 mL). The reaction mixture was stirred at room temperature for 30 minutes, poured into water, and extracted with ethyl ether. The organic extracts were dried over $MgSO_4$. Evaporation and purification by flash chromatography on silica gel (hexanes/EtAOc 8:1) gave a yellow oil (2.56 g, 89% yield): MS m/e 538 ($M^+$);

Analysis for: $C_{37}H_{30}O_4$ Calc'd: C, 82.51; H, 5.61 Found: C, 81.74; H, 5.78

Step h) (2S)-2-[4'-(2-Benzyl-benzofuran-3-yl)-biphenyl-4-yloxy]-3-phenyl-propionic acid Sodium hydroxide (2.5 N, 10 mL) was added into a mixture of (2S)-2-[4'-(2-benzyl-benzofuran-3-yl)-biphenyl-4-yloxy]-3-phenyl-propionic acid methyl ester (2.5 g, 4.65 mmol), methyl alcohol (40 mL) and tetrahydrofuran (40 mL). The reaction mixture was stirred for 1 hour, poured into water, acidified with HCl (2 N), and extracted with ethyl ether. The organic extracts were dried over $MgSO_4$. Evaporation and crystallization from ethyl ether/hexanes gave a white solid (2.32 g, 95% yield): mp 167–169; MS m/e 376 ($M^+$);

Analysis for: $C_{36}H_{28}O_4$ Calc'd: C, 82.42; H, 5.38 Found: C, 82.26; H, 5.36.

EXAMPLE 2

[(4,4''-Dimethoxy-5'-{2-(phenylmethyl)benzo[b]thien-3-yl]phenyl}[1,1';3',1''-terphenyl]-2'-yl)oxy]-acetic acid Step a) 3-(4'-Methoxy-biphenyl-4-yl)-benzo[b]thiophene Palladium (II) acetate was added into a mixture of 3-bromo-benzo[b]-thiophene (1.4 g, 6.58 mmol), 4'-methoxy-biphenyl-4-boronic acid (1.5 g, 6.58 mmol), potassium carbonate (2.27 g, 16.45 mmol), acetone (20 mL) and $H_2O$ (20 mL). The reaction mixture was stirred at 65° C. for 2 h, poured into water, and extracted with ethyl acetate. The organic extracts were dried over $MgSO_4$ Evaporation and crystallization from ethyl ether/hexanes gave an off-white solid (1.76 g, 85% yield): mp 134–136; MS m/e 316 ($M^+$);

Analysis for: $C_{21}H_{16}OS$ Calc'd: C, 79.71; H, 5.10 Found: C, 78.98; H, 5.13

Step b) 4'-Benzo[b]thiophen-3-yl-biphenyl-4-ol

This compound was prepared from 3-(4'-methoxy-biphenyl-4-yl)-benzo[b]thiophene, in substantially the same manner, as described in Example 1 step d, and was obtained as an off-white solid, mp 167–169° C.; MS m/e 302 ($M^+$);

Analysis for: $C_{20}H_{14}OS$ Calc'd: C, 79.44; H, 4.67 Found: C, 79.36; H, 4.52

Step c) [3-(4'-Hydroxy-biphenyl-4-yl)-benzo[b]thiophen-2-yl]-phenyl-methanone

This compound was prepared from 4'-benzo[b]thiophen-3-yl-biphenyl-4-ol, in substantially the same manner as described in Example 1 step e, and was obtained as a yellow solid, mp 205–207° C.; MS m/e 406 ($M^+$);

Analysis for: $C_{27}H_{18}O_2S$ Calc'd: C, 79.78; H, 4.46 Found: C, 78.95; H, 4.59

Step d) 4'-(2-Benzyl-benzo[b]thiophen-3-yl)-biphenyl-4-ol

This compound was prepared from [3-(4'-hydroxy-biphenyl-4-yl)-benzo[b]thiophen-2-yl]-phenyl-methanone, in substantially the same manner as described in Example 1 step f, and was obtained as a white solid, mp 178–180° C.; MS m/e 392 ($M^+$);

Analysis for: $C_{27}H_{20}OS$ Calc'd: C, 81.62; H, 5.14 Found: C, 81.60; H, 5.32

Step e) 4'-(2-Benzyl-benzo[b]thiophen-3-yl)-3-bromo-biphenyl-4-ol and 4'-(2-Benzyl-benzo[b]thiophen-3-yl)-3,5-dibromo-biphenyl-4-ol Bromine (1.47 mL, 28.69 mmol) in acetic acid (50 mL) was added dropwise over a 30 minutes period into a cold (5° C.) mixture of 4'-(2-benzyl-benzo[b]thiophen-3-yl)-biphenyl-4-ol (7.5 g, 19.13 mmol), potassium acetate (18.6 g, 190.13 mmol), and acetic acid (200 mL). After the addition the mixture was poured into water, and extracted with ethyl ether. The organic extracts were washed with aqueous sodium bisulfite and dried over $MgSO_4$. Evaporation and purification by flash chromatography on silica gel (hexanes/EtAOc/$CH_2Cl_2$ 3:1:1) gave 4'-(2-benzyl-benzo[b]thiophen-3-yl)-3-bromo-biphenyl-4-ol as a light yellow solid (2.4 g); mp 54–56° C. MS m/e 477 ($M^+$);

Analysis for: $C_{27}H_{19}BrOS$ Calc'd: C, 68.79; H, 4.06 Found: C, 68.37; H, 4.17 and 4'-(2-benzyl-benzo[b]thiophen-3-yl)-3,5-dibromo-biphenyl-4-ol as a light yellow solid (4.7 g); mp 59–61° C.; MS m/e 548 ($M^+$);

Analysis for: $C_{27}H_{18}Br_2OS$ Calc'd: C, 58.93; H, 3.30 Found: C, 59.21; H, 3.57

Step f) 4,4''-Dimethoxy-5'-{4-[2-(phenylmethyl)benzo[b]thien-3-yl]phenyl}-[1,1';3',1''-terphenyl]-2'-ol and 4-(2-benzyl-benzo[b]-thiophen-3-yl)-5'-bromo-4''-methoxy[1,1';3',1''-terphenyl]-4'-ol Palladium (II) acetate (81 mg, 0.036 mmol) was added into a mixture of 4'-(2-benzyl-benzo[b]thiophen-3-yl)-3,5-dibromo-biphenyl-4-ol (1.0 g, 1.82 mmol), 4-methoxy-benzeneboronic acid, barium hydroxide (0.93 g, 5.46 mmol), 1,2-dimethoxyethane (10 mL), and water (10 mL). The mixture was stirred at 75° C. for 10 hours, poured into water, and extracted with ethyl ether. The organic extracts were dried over $MgSO_4$. Evaporation and purification by flash chromatography on silica gel (hexanes/EtAOc 4:1) gave 4,4''-dimethoxy-5'-{4-[2-(phenylmethyl)benzo[b]thien-3-yl]phenyl}[1,1';3',1''-terphenyl]-2'-ol as a yellow solid (0.45 g,): mp 80–82; MS m/e 604 ($M^+$);

Analysis for: $C_{41}H_{32}O_3S$ Calc'd: C, 81.43; H, 5.33 Found: C, 80.19; H, 5.44 and 4-(2-benzyl-benzo[b]-thiophen-3-yl)-5'-bromo-4''-methoxy[1,1';3',1''-terphenyl]-4'-ol as a yellow solid (0.45 g,): mp 74–76; MS m/e 576 ($M^+$);

Analysis for: $C_{34}H_{25}O_2S$ Calc'd: C, 70.71; H, 4.36 Found: C, 69.78; H, 5.31

Step g) [(4,4''-Dimethoxy-5'-{2-(phenylmethyl)benzo[b]thien-3-yl]phenyl}-[1,1';3',1''-terphenyl]-2'-yl)oxy]-acetic acid Methyl bromoacetate (0.16 mL, 1.66 mmol) was added dropwise into a mixture of 4,4''-dimethoxy-5'-{4-[2-(phenylmethyl)benzo[b]thien-3-yl]phenyl}[1,1';3',1''-terphenyl]-2'-ol (1.0 g, 1.66 mmol), potassium carbonate (0.23 g, 1.66 mmol), and N,N-dimethylformamide (10 mL). The reaction mixture was stirred at 75° C. for 2 hours, and then poured into water and extracted with ethyl acetate. The organic extracts were dried over $MgSO_4$. Evaporation and purification by flash chromatography on silica gel (hexanes/EtAOc 4:1) gave a yellow oil (1.05 g), which was taken in methyl alcohol (10 mL) and tetrahydrofuran (10 mL), and treated with NaOH (2.5 N 3.0 mL) for 30 minutes. The new reaction mixture was poured into water, acidified with HCl (2 N), and extracted with ethyl ether. The organic extracts were dried over $MgSO_4$. Evaporation and purification by flash chromatography on silica gel (hexanes/EtAOc 3:1) gave white solid (0.79 g, 72% yield): mp 99–101; MS m/e 662 ($M^+$);

Analysis for: $C_{43}H_{34}O_5S$ Calc'd: C, 77.92; H, 5.17 Found: C, 77.03; H, 5.29.

EXAMPLE 3

[4-(2-Benzyl-benzo[b]-thiophen-3-yl)-5'-bromo-4''-methoxy[1,1';3',1''-terphenyl]-4-yl)oxy]-acetic acid The title compound was prepared from 4-(2-benzyl-benzo[b]-thiophen-3-yl)-5'-bromo-4''-methoxy[1,1';3',1''-terphenyl]-4'-ol, in substantially the same manner, as described in Example 2 step g, and was obtained as a white solid, mp 94–96° C.; MS m/e 634 ($M^+$);

Analysis for: $C_{36}H_{27}BrO_4S$ Calc'd: C, 68.03; H, 4.28 Found: C, 67.57; H, 4.29.

EXAMPLE 4

(4'-Benzofuran-3-yl-biphenyl-4-yloxy)-acetic acid

Sodium hydride (0.15 g, 3.49 mmol) was added portion-wise into a mixture of 4'-benzofuran-3-yl-biphenyl-4-ol (1.0 g, 3.49 mmol), and N,N-dimethylformamide (10 mL). The reaction mixture was stirred for 1 hour, and then methyl bromoacetate (0.49 mL, 5.23 mmol) was added dropwise. The mixture was stirred for 30 minutes, poured into water, and extracted with ethyl acetate. The organic extracts were dried over $MgSO_4$. Evaporation gave a yellow oil (1.25 g).

The residue was taken in methyl alcohol (20 mL) and tetrahydrofuran (20 mL), and treated with sodium hydroxide (2.5 N, 5.0 mL) for 30 minutes. The mixture was then poured into water, acidified with HCl (2 N) and extracted with ethyl ether. The organic extracts were dried over $MgSO_4$. Evaporation and crystallization from ethyl ether/hexanes gave a white solid (0.38 g, 32% yield): mp 196–197; MS m/e 344 (M$^+$);

Analysis for: $C_{22}H_{16}O_4$ Calc'd: C, 76.73; H, 4.68 Found: C, 76.63; H, 4.58.

EXAMPLE 5

2-(4'-Benzofuran-3-yl-biphenyl-4-yloxy)-3-phenyl-propionic acid

The title compound was prepared from 4'-benzofuran-3-yl-biphenyl-4-ol, in substantially the same manner, as described in Example 2 step g, and was obtained as a white solid, mp 142–143° C.; MS m/e 434 (M$^+$);

Analysis for: $C_{29}H_{22}O_4$ Calc'd: C, 80.17; H, 5.10 Found: C, 80.54; H, 5.09.

EXAMPLE 6

[4'-(2-Bromo-benzofuran-3-yl)-biphenyl-4-yloxy]-acetic acid

Step a) 2-Bromo-3-(4'-methoxy-biphenyl-4-yl)-benzofuran

Bromine (0.29 mL, 5.67 mmol) in acetic acid (50 mL) was added dropwise over a 30 minutes period into a cold (5° C.) mixture of 3-(4'-methoxy-biphenyl-4-yl)-benzofuran (1.7 g, 5.67 mmol), potassium acetate (5.55 g, 56.7 mmol), and acetic acid (20 mL). After the addition, the mixture was poured into water, and extracted with ethyl ether. The organic extracts were washed with aqueous sodium bisulfite and dried over $MgSO_4$. Evaporation and crystallization gave an off-white solid (1.69 g, 79% yield): mp 136–137° C. MS m/e 378 (M$^+$);

Analysis for: $C_{21}H_{15}BrO_2$ Calc'd: C, 66.51; H, 3.99 Found: C, 66.17; H, 3.84

Step b) 4'-(2-Bromo-benzofuran-3-yl)-biphenyl-4-ol

This compound was prepared from 2-bromo-3-(4'-methoxy-biphenyl-4-yl)-benzofuran, in substantially the same manner, as described in Example 1 step d, and was obtained as a white solid, mp 150–151° C.; MS m/e 364 (M$^+$);

Analysis for: $C_{20}H_{13}BrO_2$ Calc'd: C, 65.77; H, 3.59 Found: C, 65.47; H, 3.46

Step c) [4'-(2-Bromo-benzofuran-3-yl)-biphenyl-4-yloxy]-acetic acid

This compound was prepared from 4'-(2-bromo-benzofuran-3-yl)-biphenyl-4-ol, in substantially the same manner, as described in Example 4, and was obtained as a white solid, mp 178–180° C.; MS m/e 423 (M$^+$);

Analysis for: $C_{22}H_{15}BrO_4$ Calc'd: C, 62.43; H, 3.57 Found: C, 61.68; H, 3.42.

EXAMPLE 7

2-[4'-(2-Bromo-benzofuran-3-yl)-biphenyl-4-yloxy]-3-phenyl-propionic acid

The title compound was prepared from 4'-(2-bromo-benzofuran-3-yl)-biphenyl-4-ol and 3-phenyllactic acid methyl ester, in substantially the same manner, as described in Example 1, steps g–h, and was obtained as a white solid, mp 148–149° C.; MS m/e 512 (M$^+$);

Analysis for: $C_{29}H_{21}BrO_4$ Calc'd: C, 67.85; H, 4.12 Found: C, 67.68; H, 4.31.

EXAMPLE 8

4'-(2-Butyl-benzofuran-3-yl)-biphenyl-4-ol

The title compound was prepared from 4'-benzofuran-3-yl-biphenyl-4-ol and N-methoxy-N-methyl-n-butylamide, in substantially the same manner, as described in Example 1, steps e–f, and was obtained as a white solid, mp 128–129° C.; MS m/e 342 (M$^+$);

EXAMPLE 9

[4'-(2-Butyl-benzofuran-3-yl)-biphenyl-4-yloxy]-acetic acid

The title compound was prepared from 4'-(2-butyl-benzofuran-3-yl)-biphenyl-4-ol, in substantially the same manner, as described in Example 4, and was obtained as a white solid, mp 126–128° C.; MS m/e 400 (M$^+$);

Analysis for: $C_{26}H_{24}O_4$ Calc'd: C, 77.98; H, 6.04 Found: C, 77.80; H, 6.06.

EXAMPLE 10

2-[4'-(2-Butyl-benzofuran-3-yl)-biphenyl-4-yloxy]-3-phenyl-propionic acid

The title compound was prepared from 4'-(2-butyl-benzofuran-3-yl)-biphenyl-4-ol, and 3-phenyllactic acid methyl ester, in substantially the same manner, as described in Example 1, steps g–h, and was obtained as a white solid, mp 169–170° C.; MS m/e 491 (M+H)$^+$;

Analysis for: $C_{33}H_{30}O_4$ Calc'd: C, 80.79; H, 6.16 Found: C, 80.75; H, 6.12.

EXAMPLE 11

2-[4'-(2-Benzyl-benzofuran-3-yl)-biphenyl-4-yloxy]-3-phenyl-propionic acid

The title compound was prepared from 4'-(2-benzyl-benzofuran-3-yl)-biphenyl-4-ol, and 3-phenyllactic acid methyl ester, in substantially the same manner, as described in Example 1, steps g–h, and was obtained as a white solid, mp 164–166° C.; MS m/e 524 (M$^+$);

Analysis for: $C_{36}H_{28}O_4$ Calc'd: C, 82.42; H, 5.38 Found: C, 82.14; H, 5.20.

EXAMPLE 12

2-[4'-(2-Butyl-benzo[b]thiopen-3-yl)-biphenyl-4-yloxy]-3-phenyl-propionic acid

The title compound was prepared from 4'-(2-butyl-benzo[b]-thiophen-3-yl)-biphenyl-4-ol, and 3-phenyllactic acid methyl ester, in substantially the same manner, as described in Example 1, steps g–h, and was obtained as a white solid, mp 159–161° C.; MS m/e 507 (M+H)$^+$;

Analysis for: $C_{33}H_{30}O_3S$ Calc'd: C, 78.23; H, 5.97 Found: C, 78.12; H, 6.02.

EXAMPLE 13

2-[4'-(2-Benzyl-benzo[b]thiophen-3-yl)-biphenyl-4-yloxy]-3-phenyl-propionic acid The title compound was prepared from 4'-(2-benzyl-benzo[b]-thiophen-3-yl)-biphenyl-4-ol, and 3-phenyllactic acid methyl ester, in substantially the same manner, as described in Example 1, steps g–h, and was obtained as a white solid, mp 165–167° C.; MS m/e 540 (M$^+$);

Analysis for: $C_{36}H_{28}O_3S$ Calc'd: C, 79.97; H, 5.22 Found: C, 79.96; H, 5.38.

EXAMPLE 14

2-[4'-(2-Benzoyl-benzofuran-3-yl)-biphenyl-4-yloxy]-3-phenyl-propionic acid

The title compound was prepared from 4'-(2-benzoyl-benzofuran-3-yl)-biphenyl-4-ol, and 3-phenyllactic acid methyl ester, in substantially the same manner, as described in Example 1, steps g–h, and was obtained as a yellow solid, mp 159–161° C.; MS m/e 538 (M$^+$);

Analysis for: $C_{36}H_{26}O_5$ Calc'd: C, 80.28; H, 4.86 Found: C, 80.15; H, 4.91.

EXAMPLE 15

(2R)-2-[4'-(2-Benzyl-benzofuran-3-yl)-biphenyl-4-yloxy]-3-phenyl-propionic acid

The title compound was prepared from 4'-(2-benzyl-benzofuran-3-yl)-biphenyl-4-ol, and (S)-(−)-3-phenyllactic acid methyl ester, in substantially the same manner, as described in Example 1, steps g–h, and was obtained as a white solid, mp 167–169° C.; MS m/e 524 (M$^+$);

Analysis for: $C_{36}H_{28}O_4$ Calc'd: C, 82.42; H, 5.38 Found: C, 82.43; H, 5.53.

EXAMPLE 16

(2S)-2-[4'-(2-Benzyl-benzofuran-3-yl)-biphenyl-4-yloxy]-3-phenyl-propionic acid tromethamine salt A mixture of (2S)-2-[4'-(2-benzyl-benzofuran-3-yl)-biphenyl-4-yloxy]-3-phenyl-propionic acid (1.0 g, 1.91 mmol), tromethamine (0.23 g, 1.91 mmol), tetrahydrofuran (10 mL), and water (1.0 mL) was stirred at 60° C. for 1 hour. The volatiles were removed in vacuo and the residue was washed with water and dried to give a white solid (1.1 g, 89% yield); mp 147–148; MS m/e 523 (M–H)$^+$;

Analysis for: $C_{36}H_{27}O_4$·tromethamine×1.5 $H_2O$ Calc'd: C, 71.41; H, 6.29; N, 2.08 Found: C, 71.33; H, 6.35; N, 2.40.

EXAMPLE 17

(2R)-2-[4'-(2-Benzyl-benzofuran-3-yl)-biphenyl-4-yloxy]-propionic acid

The title compound was prepared from 4'-(2-benzyl-benzofuran-3-yl)-biphenyl-4-ol, and (S)-(+)-lactic acid methyl ester, in substantially the same manner, as described in Example 1, steps g–h, and was obtained as a white solid, mp 112–114° C.; MS m/e 448 (M$^+$);

Analysis for: $C_{30}H_{24}O_4$ Calc'd: C, 80.34; H, 5.39 Found: C, 79.86; H, 5.73.

EXAMPLE 18

(2R)-2-[4'-(2-Benzyl-benzofuran-3-yl)-biphenyl-4-yloxy]-phenyl-acetic acid

The title compound was prepared from 4'-(2-benzyl-benzofuran-3-yl)-biphenyl-4-ol, and (S)-(+)-mandelic acid methyl ester, in substantially the same manner, as described in Example 1, steps g–h, and was obtained as a white solid, mp 177–179° C.; MS m/e 509 (M–H)$^+$;

Analysis for: $C_{35}H_{26}O_4$×0.4 $H_2O$ Calc'd: C, 81.19; H, 5.22 Found: C, 81.34; H, 5.46.

EXAMPLE 19

(2R)-2-{4'-[2-(4-Fluoro-benzyl-benzo[b]thiophene-3-yl)-biphenyl-4-yloxy]-3-phenyl-propionic acid Step a) (4-Fluoro-phenyl)-[3-(4'-methoxy-biphenyl-4-yl)-benzo[b]thiophen-2-yl]-methanol This compound was prepared from 3-(4'-methoxy-biphenyl-4-yl)-benzo[b]thiophene, and 4-fluoro-benzaldehyde, in substantially the same manner, as described in Example 1, step e, and was obtained as a white solid, mp 66–68° C.; MS m/e 440 (M$^+$);

Analysis for: $C_{28}H_{21}FO_2S$ Calc'd: C, 76.34; H, 4.81 Found: C, 75.82; H, 4.89

Step b) 2-(4-Fluoro-benzyl)-3-(4'-methoxy-biphenyl-4-yl)-benzo[b]-thiophene

Trifluoroacetic acid (5 mL) was added dropwise into a mixture of (4-fluoro-phenyl)-[3-(4'-methoxy-biphenyl-4-yl)-benzo[b]thiophen-2-yl]-methanol (1.2 g, 2.72 mmol), sodium borohydride (0.51 g, 13.75 mmol), and ethyl ether (10 mL). The reaction mixture was stirred for 30 minutes, poured into water, basified with sodium hydroxide (2 N), and extracted with ethyl ether. The organic extracts were dried over MgSO$_4$. Evaporation and crystallization from ethyl ether/hexanes gave a white solid (1.02 g, 88% yield): mp 100–102; MS m/e 424 (M$^+$);

Step c) (2R)-2-{4'-[2-(4-Fluoro-benzyl-benzo[b]thiophene-3-yl)-biphenyl-4-yloxy]-3-phenyl-propionic acid This compound was prepared from 2-(4-fluoro-benzyl)-3-(4'-methoxy-biphenyl-4-yl)-benzo[b]-thiophene, in substantially the same manner, as described in Example 1 step d, and g–h, and was obtained as a white solid, mp 151–153° C.; MS m/e 558 (M$^+$);

Analysis for: $C_{36}H_{26}FO_3S$ Calc'd: C, 77.40; H, 4.87 Found: C, 77.55; H, 4.58.

EXAMPLE 20

(2R)-2-{4'-[2-(4-Methoxy-benzyl-benzo[b]thiophene-3-yl)-biphenyl-4-yloxy]-3-phenyl-propionic acid The title compound was prepared from 3-(4'-methoxy-biphenyl-4-yl)-benzo[b]thiophene, and 4-methoxy-benzaldehyde in substantially the same manner, as described in Example 19, and was obtained as a white solid, mp 75–77° C.; MS m/e 569 (M–H)$^+$;

Analysis for: $C_{37}H_{30}O_4S$ Calc'd: C, 77.87; H, 5.30 Found: C, 76.57; H, 5.39.

EXAMPLE 21

[4'-(2-Butyl-benzo[b]thiophene-3-yl)-biphenyl-4-yloxy]-phenyl-acetic acid

The title compound was prepared from 4'-(2-butyl-benzofuran-3-yl)-biphenyl-4-ol, and mandelic acid methyl ester, in substantially the same manner, as described in Example 1, steps g–h, and was obtained as a white solid, mp 157–159° C.; MS m/e 493 (M+H)$^+$;

Analysis for: $C_{32}H_{28}O_3S$ Calc'd: C, 78.02; H, 5.73 Found: C, 77.67; H, 5.91.

EXAMPLE 22

(2R)-2-{4'-[2-(Hydroxy-phenyl-methyl)-benzofuran-3-yl)-biphenyl-4-yloxy]-3-phenyl-propionic acid Sodium borohydride (0.15 g, 4.06 mmol) was added portionwise into a cold (0° C.) mixture of (2R)-2-[4'-(2- benzoyl-benzofuran-3-yl)-biphenyl-4-yloxy]-3-phenyl-propionic acid methyl ester (1.5, 2.7 mmol), methyl alcohol (20 mL) and tetrahydrofuran (5 mL). The reaction mixture was allowed to come to room temperature and stirred for 30 minutes. The mixture was then poured into water, acidified with HCl (2 N), and extracted with ethyl acetate. The organic extracts were dried over $MgSO_4$. Evaporation gave a yellow oil (1.4 g), which was taken in methyl alcohol (20 mL), tetrahydrofuran (20 mL), and treated with sodium hydroxide (2.5 N, 5.0 mL) for 30 minutes. The mixture was poured into water, acidified with HCl (2 N) and extracted with ethyl ether. The organic extracts were dried over $MgSO_4$. Evaporation and purification by flash chromatography on silica gel (hexanes/EtAOc 5:1) gave an off-white solid (1.16 g, 79% yield): mp 95–97; MS m/e 539 $(M-H)^+$;

Analysis for: $C_{36}H_{28}O_5$ Calc'd: C, 79.98; H, 5.22 Found: C, 79.92; H, 5.34.

EXAMPLE 23

(2S)-2-[4'-(2-Benzyl-benzofuran-3-yl)-biphenyl-4-yloxy]-3-phenyl-propionic acid methyl ester The title compound was prepared from 4'-(2-benzyl-benzofuran-3-yl)-biphenyl-4-ol, in substantially the same manner, as described in Example 1, step g, and was obtained as a white solid, mp 67–69° C.; MS m/e 538 $(M^+)$;

Analysis for: $C_{37}H_{30}O_4$ Calc'd: C, 82.51; H, 5.61 Found: C, 81.74; H, 5.78.

EXAMPLE 24

2-[4'-(2-Benzyl-benzofuran-3-yl)-biphenyl-4-yloxy]-2-methyl-3-phenyl-propionic acid Step a) 2-[4'-(2-benzyl-benzofuran-3-yl)-biphenyl-4-yloxy]-2-methyl-3-phenyl-propionic acid ethyl ester 2-Bromo-propionic acid ethyl ester (1.28 mL, 9.84 mmol) was added dropwise into a mixture of 4'-(2-benzyl-benzofuran-3-yl)-biphenyl-4-ol (3.7 g, 9.48 mmol), potassium carbonate (1.49 g, 10.82 mmol), and N,N-dimethylformamide (10 mL). The reaction mixture was stirred at 70° C. for 10 hours, poured in to water, acidified with HCl (2 N), and extracted with ethyl acetate. The organic extracts were dried over $MgSO_4$. Evaporation and purification by flash chromatography on silica gel (hexanes/EtAOc 10:1) gave a viscous clear oil (4.2 g, 96% yield): MS m/e 476 $(M^+)$;

Analysis for: $C_{32}H_{28}O_4 \times 0.2$ $H_2O$ Calc'd: C, 80.04; H, 5.96 Found: C, 80.03; H, 6.01

Step b) 2-[4'-(2-benzyl-benzofuran-3-yl)-biphenyl-4-yloxy]-2-methyl-3-phenyl-propionic acid Lithium bis(trimethylsilyl)amide (1.0 M, 1.68 mL, 1.68 mmol) was added dropwise into a cold (−78° C.) mixture of 2-[4'-(2-benzyl-benzofuran-3-yl)-biphenyl-4-yloxy]-2-methyl-3-phenyl-propionic acid ethyl ester (0.8 g, 1.68 mmol), and tetrahydrofuran (8.0 mL). The mixture was allowed to gradually warm up to −45° C., and stirred for 2 hours. Benzyl bromide (0.29 mL, 2.52 mmol) was added into the reaction mixture. The temperature was gradually raised to room temperature and the reaction was stirred for 15 hours. The mixture was then poured in to water, acidified with HCl (2 N) to pH=5, and extracted with ethyl acetate. The organic extracts were dried over $MgSO_4$. Evaporation and purification by flash chromatography on silica gel (hexanes/EtAOc 5:1) gave an clear oil (0.43 g). The product was saponified according to Example 1 step h, to give a white solid (0.32 g, 34% yield for two steps): MS m/e 538 $(M^+)$;

Analysis for: $C_{37}H_{30}O_4$ Calc'd: C, 81.68; H, 5.67 Found: C, 81.66; H, 5.69.

EXAMPLE 25

(2R)-2-{4'-[2-(3,4-Dimethoxy-benzyl)-benzo[b]thiophen-3-yl]-biphenyl-4-yloxy}-3-phenyl-propionic acid The title compound was prepared from 4'-(2-benzyl-benzo[b]thiophen-3-yl)-biphenyl-4-ol, and 3,4-dimethoxy-benzaldehyde in substantially the same manner, as described in Example 20, and was obtained as a white solid, mp 59–61° C.; MS m/e 599 $(M-H)^+$;

Analysis for: $C_{38}H_{22}O_5S \times 1.5$ $H_2O$ Calc'd: C, 72.70; H, 5.62 Found: C, 72.40; H, 5.50.

EXAMPLE 26

(2R)-2-{4'-[2-(2,4-Dimethoxy-benzyl)-benzo[b]thiophen-3-yl]-biphenyl-4-yloxy}-3-phenyl-propionic acid The title compound was prepared from 4'-(2-benzyl-benzo[b]thiophen-3-yl)-biphenyl-4-ol, and 2,4-dimethoxy-benzaldehyde in substantially the same manner, as described in Example 20, and was obtained as a white solid, mp 70–72° C.; MS m/e 599 $(M-H)^+$;

Analysis for: $C_{38}H_{22}O_5S \times 0.5$ $H_2O$ Calc'd: C, 74.85; H, 5.37 Found: C, 74.80; H, 5.44.

EXAMPLE 27

(2R) 2-{4'-[2-(2,2-Dimethyl-benzo[1,3]dioxol-5-ylmethyl)-benzo[b]thiophene-3-yl)-biphenyl-4-yloxy]-3-phenyl-propionic acid Step a) 4-[3-(4'-Hydroxy-biphenyl-4-yl)-benzo[b]thiophen-2-ylmethyl]-benzene-1,2-diol This compound was prepared from 4'-[2-(2,4-dimethoxy-benzyl)-benzo[b]thiophen-3-yl]-biphenyl-4-ol, in substantially the same manner, as described in Example 1 step d, and was obtained as a white solid, mp 148–150° C.; MS m/e 452 $(M^+)$;

Analysis for: $C_{29}H_{24}O_3S \times 0.5$ $H_2O$ Calc'd: C, 75.46; H, 5.46 Found: C, 75.53; H, 5.41

Step b) 4'-[2-(2,2-Dimethyl-benzo[1,3]dioxol-5-ylmethyl)-benzo[b]thiophene-3-yl)-biphenyl-4-ol Camphorsulfonic acid (0.2 g) was added into a mixture of 4-[3-(4'-hydroxy-biphenyl-4-yl)-benzo[b]thiophen-2-ylmethyl]-benzene-1,2-diol (1.4 g, 3.3 mmol), and 2,2-dimethoxy propane (5.0 mL). The reaction mixture was stirred at 40° C. for 24 hours, poured into water, and extracted with ethyl ether. The organic extracts were washed with aqueous sodium bicarbonate, and then dried over $MgSO_4$. Evaporation and purification by flash chromatography on silica gel (hexanes/EtAOc 4:1) gave a gray solid (1.19 g, 72% yield): mp 58–60° C.; MS m/e 464 $(M^+)$;

Analysis for: $C_{30}H_{24}O_3S \times 1$ $H_2O$ Calc'd: C, 74.66; H, 5.43 Found: C, 74.53; H, 5.74

Step c) (2R) 2-{4'-[2-(2,2-Dimethyl-benzo[1,3]dioxol-5-ylmethyl)-benzo[b]thiophene-3-yl)-biphenyl-4-yloxy]-3-phenyl-propionic acid This compound was prepared from 4'-[2-(2,2-dimethyl-benzo[1,3]dioxo-5-ylmethyl)-benzo[b]thiophene-3-yl)-biphenyl-4-ol, and (S)-(−)-3-phenyllactic acid methyl ester in substantially the same manner, as described in Example 1 steps g–h, and was obtained as a white solid, mp 68–70° C.; MS m/e 611 $(M-H)^+$;

33

Analysis for: $C_{39}H_{32}O_5S\times0.5$ $H_2O$ Calc'd: C, 75.34; H, 5.35 Found: C, 75.35; H, 5.35

EXAMPLE 28

(2R)-2-{4'-[2-(3, 4-Dihydroxy-benzyl)-benzo[b]thiophene-3-yl)-biphenyl-4-yloxy]-3-phenyl-propionic acid A mixture of (2R) 2-{4'-[2-(2,2-dimethyl-benzo[1,3]dioxol-5-ylmethyl)-benzo[b]thiophene-3-yl)-biphenyl-4-yloxy]-3-phenyl-propionic acid (0.38 g, 0.62 mmol), tetrahydrofuran (30 mL) and HCl (2 N, 5.0 mL) was stirred at 50° C. for 10 hours. The reaction mixture was then poured into water, and extracted with ethyl ether. The organic extracts were dried over $MgSO_4$. Evaporation and purification by flash chromatography on acidic silica gel (hexanes/EtAOc 2:1) gave a pink solid (0.26 g, 72% yield): mp 108–110° C.; MS m/e 571 (M–H)$^+$;

Analysis for: $C_{36}H_{28}O_5S\times0.5$ $H_2O$ Calc'd: C, 74.33; H, 5.03 Found: C, 74.22; H, 5.28.

EXAMPLE 29

(2R)-2-[4'-(2-Benzyl-thiophene-3-yl)-biphenyl-4-yloxy]-3-phenyl-propionic acid

Step a) 3-(4'-Methoxy-biphenyl-4-yl)-thiophene-2-carboxaldehyde

This compound was prepared from 3-bromo-thiophene-2-carboxaldehyde and 4'-methoxy-biphenyl-4-boronic acid in substantially the same manner, as described in Example 2 step a, and was obtained as an off-white solid, mp 139–141° C.; MS m/e 294 (M$_+$);

Analysis for: $C_{18}H_{14}O_2S$ Calc'd: C, 73.44; H, 4.79 Found: C, 73.37; H, 4.77

Step b) [3-(4'-Methoxy-biphenyl-4-yl)-thiophen-2yl]-phenyl-methanol

Phenyl magnesium bromide (2 M, 13.6 mL, 27.21 mmol) was added dropwise into a cold (0° C.) mixture of 3-(4'-methoxy-biphenyl-4-yl)-thiophene-2-carboxaldehyde (8.0 g, 27.21 mmol), and tetrahydrofuran (100 mL). The reaction mixture was stirred for 30 minutes, and then quenched with aqueous ammonium chloride, poured into water and extracted with ethyl acetate. The organic extracts were dried over $MgSO_4$. Evaporation and purification by flash chromatography on silica gel (hexanes/EtAOc 4:1) gave an off-white solid (7.2 g, 71% yield): mp 115–117° C.; MS m/e 372 (M$^+$);

Analysis for: $C_{24}H_{20}O_2S$ Calc'd: C, 77.39; H, 5.41 Found: C, 77.12; H, 5.48

Step c) (2R)-2-[4'-(2-Benzyl-thiophene-3-yl)-biphenyl-4-yloxy]-3-phenyl-propionic acid This compound was prepared from [3-(4'-methoxy-biphenyl-4-yl)-thiophen-2yl]-phenyl-methanol in substantially the same manner, as described in Example 19 step b, and Example 1 steps d–h, and was obtained as a white solid, mp 152–154° C.; MS m/e 489 (M–H)$^+$;

Analysis for: $C_{32}H_{26}O_3S$ Calc'd: C, 78.34; H, 5.34 Found: C, 78.32; H, 5.52.

EXAMPLE 30

3-Phenyl-2-[4'-(2-thiazole-2-ylmethyl-benzo[b]thiophene-3-yl)-biphenyl-4-yloxy]-propionic acid Step a) 4'(2-Thiazole -2-yl-methyl-benzo[b]thiophen-3-yl)-biphenyl-4-ol This compound was prepared from 4'-benzo[b]thiophen-3-yl-biphenyl-4-ol and thiazole-2-carboxaldehyde in substantially the same manner, as described in Example 1 step e, and Example 19 step b (with the modification of using triethylsilane in place of sodium borohydride as the reducing agent), and was obtained as a light yellow solid, mp 208–210° C.; MS m/e 399 (M$^+$);

Analysis for: $C_{24}H_{17}NOS_2\times0.5$ $H_2O$ Calc'd: C, 70.56; H, 4.44; N, 3.43 Found: C, 70.60; H, 4.36; N, 3.35

Step b) 3-Phenyl-2-[4'-(2-thiazole-2-ylmethyl-benzo[b]thiophene-3-yl)-biphenyl-4-yloxy]-propionic acid This compound was prepared from 4'(2-thiazole -2-yl-methyl-benzo[b]thiophen-3-yl)-biphenyl-4-ol, and (S)-(–)-3-phenyllactic acid methyl ester, in substantially the same manner, as described in Example 1, steps g–h, and was obtained as a white solid, mp 85–88° C.; MS m/e 547 (M$^+$);

Analysis for: $C_{33}H_{25}NO_3S_2\times1$ $H_2O$ Calc'd: C, 70.06; H, 4.81; N, 2.48 Found: C, 69.81; H, 4.80; N, 2.68.

EXAMPLE 31

(2S)-2-[4'-(2-Benzyl-furo[2,3]pyridin-3-yl)-biphenyl-4-yloxy]-3-phenyl-propionic acid Step a) 4'-(2-Benzyl-furo[2,3-b]pyridin-3-yl)-biphenyl-4-ol This compound was prepared from 3-bromo-2-benzyl-furo[2,3-b]pyridine, in substantially the same manner, as described in Example 2, steps e and a, and Example 1 step d, and was obtained as an off-white solid, mp 185–186° C.; MS m/e 386 (M$^+$);

Analysis for: $C_{26}H_{19}NO_2\times0.4$ $H_2O$ Calc'd: C, 81.18; H, 5.19; N, 3.64 Found: C, 81.18; H, 5.14; N, 3.47

Step b) (2S)-2-[4'-(2-Benzyl-furor2,3]pyridin-3-yl)-biphenyl-4-yloxy]-3-phenyl-propionic acid potassium salt This compound was prepared from 4'-(2-benzyl-furo[2,3-b]pyridin-3-yl)-biphenyl-4-ol, and (R)-(+)-3-phenyllactic acid methyl ester, in substantially the same manner, as described in Example 1, steps g–h. In step h the hydrolysis was done with potassium hydroxide, and removal of the solvents gave the desired product. The product was obtained as an off-white solid, mp 85–88° C.; MS m/e 593 (M$^+$);

Analysis for: $C_{33}H_{26}NO_4K\times1.2$ $H_2O$ Calc'd: C, 71.82; H, 4.89; N, 2.39 Found: C, 71.84; H, 4.93; N, 2.13.

EXAMPLE 32

(2R)-3-phenyl-2-[4'-(2-pyridin-2-ylmethyl-benzo[b]thiophene-3-yl)-biphenyl-4-yloxy]-propionic acid sodium salt The title compound was prepared from 4'-benzo[b]thiophen-3-yl-biphenyl-4-ol and pyridine-2 carboxaldehyde, in substantially the same manner, as described in Example 2, steps e and a, and Example 30, and was obtained as a white solid; MS m/e 540 (M–H)$^+$;

Analysis for: $C_{33}H_{26}NO_3SNa\times1$ $H_2O$ Calc'd: C, 72.29; H, 4.81; N, 2.41 Found: C, 72.67; H, 4.66; N, 2.41.

EXAMPLE 33

(2R)-3-phenyl-2-[4'-(2-pyridin-2-ylmethyl-benzo[b]thiophene-3-yl -biphenyl-4-yloxy]-propionic acid The title compound was prepared from 4'-benzo[b]thiophen-3-yl-biphenyl-4-ol and pyridine-2 carboxaldehyde, in substantially the same manner, as described in Example 2, steps e and a, and Example 30, and was obtained as a white solid; MS m/e 540 (M–H)$^+$;

Analysis for: $C_{35}H_{27}NO_3S\times0.5$ $H_2O$ Calc'd: C, 76.36; H, 5.09; N, 2.54 Found: C, 776.46; H, 5.14; N, 2.29.

EXAMPLE 34

4'-(2-Benzyl benzo[b]thiophen-3-yl)-3-bromo-biphenyl-4-ol

The title compound was prepared from 4'-benzo[b]thiophen-3-yl-biphenyl-4-ol in substantially the same manner, as described in Example 1 steps e, was and obtained as a light yellow solid (2.4 g): mp 54–56° C. MS m/e 477 (M+);

Analysis for: $C_{27}H_{19}BrOS$ Calc'd: C, 68.79; H, 4.06 Found: C, 68.37; H, 4.17.

EXAMPLE 35

4'-(2-Benzyl-benzo[b]thiophen-3-yl)-3,5-dibromo-biphenyl-4-ol

The title compound was prepared from 4'-benzo[b]thiophen-3-yl-biphenyl-4-ol in substantially the same manner, as described in Example 1 steps e, was and obtained as a light yellow solid (4.7 g); mp 59–61° C.; MS m/e 548 (M+);

Analysis for: $C_{27}H_{18}Br_2OS$ Calc'd: C, 58.93; H, 3.30 Found: C, 59.21; H, 3.57.

EXAMPLE 36

(2R)-2-[4'-(2-Benzyl-benzo[b]thiophene-3-yl)-3-bromo-biphenyl-4-yloxy]-3-phenyl-propionic acid The title compound was prepared from 4'-(2-benzyl-benzofuran-3-yl)-3-bromo-biphenyl-4-ol, and (S)-(−)-3-phenyllactic acid methyl ester, in substantially the same manner, as described in Example 1, steps g–h , and was obtained as a white solid, mp 81–83° C.; MS m/e 618 (M+);

Analysis for: $C_{36}H_{27} BrO_3S$ Calc'd: C, 69.79; H, 4.39 Found: C, 69,39; H, 4.40.

EXAMPLE 37

(2R)-2-[4'-(2-Benzyl-benzo[b]thiophene-3-yl)-3,5-dibromo-biphenyl-4-yloxy]-3-phenyl-propionic acid The title compound was prepared from 4'-(2-benzyl-benzo[b]thiophen-3-yl)-3,5-dibromo-biphenyl-4-ol, and (S)-(−)-3-phenyllactic acid methyl ester, in substantially the same manner, as described in Example 1, steps g–h , and was obtained as a white solid, mp 87–89° C.; MS m/e 696 (M+);

Analysis for: $C_{36}H_{26}Br_2O_3S$ Calc'd: C, 61.91; H, 3.75 Found: C, 69.99; H, 3.86.

EXAMPLE 38

(2R)-2-[4-(2-Benzyl-benzo[b]thiophene-3-yl)-4"-methoxy-[1,1';3',1"]terphenyl-4'-yloxy]-3-phenyl-propionic acid The title compound was prepared from 4-(2-benzyl-benzo[b]thiophene-3-yl)-4"-methoxy-[1,1';3',1"]terphenyl-4'-ol, and (S)-(−)-3-phenyllactic acid methyl ester, in substantially the same manner, as described in Example 1, steps g–h , and was obtained as a white solid, mp 82–84° C.; MS m/e 645 (M–H)+;

Analysis for: $C_{43}H_{34} O_4S$ Calc'd: C, 79.85; H, 5.30 Found: C, 79.67; H, 5.79.

EXAMPLE 39

[4'-(2-Benzyl-benzo[b]thiophene-3-yl)-3,5-dibromo-biphenyl-4-yloxy]-acetic acid

The title compound was prepared from 4'-(2-benzyl-benzo[b]thiophen-3-yl)-3,5-dibromo-biphenyl-4-ol, and methyl bromoacetate, in substantially the same manner, as described in Example 2 step g , and was obtained as an off-white solid, mp 183–185° C.; MS m/e 606 (M+);

Analysis for: $C_{29}H_{20}Br_2O_3S$ Calc'd: C, 57.26; H, 3.31 Found: C, 57.42; H, 3.53.

EXAMPLE 40

[4'-(2-Benzyl-benzo[b]thiophene-3-yl)-3-bromo-biphenyl-4-yloxy]-acetic acid

The title compound was prepared from 4'-(2-benzyl-benzo[b]thiophen-3-yl)-3-bromo-biphenyl-4-ol, and methyl bromoacetate, in substantially the same manner, as described in Example 2 step g , and was obtained as a white solid, mp 150–152° C.; MS m/e 528 (M+);

Analysis for: $C_{29}H_{20}Br_2O_3S$ Calc'd: C, 65.79; H, 4.00 Found: C, 65.50; H, 4.29.

EXAMPLE 41

(2S)2-[4'-(2-Benzyl-benzo[b]-thiophen-3-yl)-3,5-dibromo-biphenyl-4-yloxy]-4-phenyl-butyric acid The title compound was prepared from 4'-(2-benzyl-benzo[b]thiophen-3-yl)-3,5-dibromo-biphenyl-4-ol, and (R)-(−)-2-hydroxy-4-phenylbutyric acid methyl ester, in substantially the same manner, as described in Example 1, steps g–h , and was obtained as a white solid, mp 85–87° C.; MS m/e 709 (M–H)+;

Analysis for: $C_{37}H_{28}Br_2O_3S$ Calc'd: C, 62.37; H, 3.96 Found: C, 62.03; H, 4.06.

EXAMPLE 42

4-[4'-(2-Benzyl-benzo[b]thiophen-3-yl)-3-bromo-biphenyl-4-yloxy -butyric acid

The title compound was prepared from 4'-(2-benzyl-benzo[b]thiophen-3-yl)-3-bromo-biphenyl-4-ol, and 4-bromobutyric acid methyl aster, in substantially the same manner, as described in Example 2 step g, and was obtained as a white solid, mp 135–137° C.; MS m/e 555 (M–H)+;

Analysis for: $C_{31}H_{25}BrO_3S \times 0.3 H_2O$ Calc'd: C, 66.01; H, 4.54 Found: C, 66.13; H, 4.78.

EXAMPLE 43

(2R)-2-[4'-(2-Benzyl-benzo[b]-thiophen-3-yl)-3,5-dibromo-biphenyl-4-yloxy]-4-(1,3-dioxo-1,3-dihydro-isoindol-2-yl)-butyric acid Step a) (2R)-2-[4'-(2-Benzl-benzo[b]-thiophen-3-yl)-3,5-dibromo-biphenyl-4-yloxy]-4-(1,3-dioxo-1,3-dihydro-isoindol-2-yl)-butyric acid methyl ester This compound was prepared from 4'-(2-benzyl-benzo[b]thiophen-3-yl)-3,5-dibromo-biphenyl-4-ol, and (S)-(+)-a-1,3-dioxo-2-isoindolinebutyric acid methyl ester, in substantially the same manner, as described in Example 1 step g, and was obtained as a light yellow oil (1.2 g, 83% yield); MS m/e 793 (M+);

Step b) (2R)-2-[4'-(2-Benzyl-benzorb]-thiophen-3-yl)-3,5-dibromo-biphenyl-4-yloxy]-4-(1,3-dioxo-1,3-dihydro-isoindol-2-yl)-butyric acid Trimethylsilyl iodide (0.29 mL, 2.07 mmol) was added into a mixture of (2R)-2-[4'-(2-benzyl-benzo[b]-thiophen-3-yl)-3,5-dibromo-biphenyl-4-yloxy]-4-(1,3-dioxo-1,3-dihydro-isoindol-2-yl)-butyric acid methyl ester (1.1 g, 1.38 mmol), and methylene chloride (10 mL). The reaction mixture was stirred at 50° C. for 24 hours. An additional 0.29 mL of trimethylsilyl iodide was added and the mixture was stirred for 48 hours, poured into water and extracted with ethyl acetate. The organic extracts were washed with aqueous sodium bisulfite and dried over $MgSO_4$. Evaporation and purification by flash chromatography on silica gel (hexanes/EtAOc 2:1) gave white solid (0.92 g, 94% yield): mp 113–115° C.; MS m/e 778 (M−H)⁺;

Analysis for: $C_{39}H_{27}Br_2NO_5S$ Calc'd: C, 59.94; H, 3.48; N, 1.79 Found: C, 59.98; H, 3.77; N, 1.74.

EXAMPLE 44

N-{(3R)-3-[4'-(2-benzyl-benzo[b]thiophen-3-yl)-3,5-dibromo-biphenyl-4-yloxvy-3-methoxycarbonyl-propyl]-phthalamic acid Potassium carbonate (0.01 g) was added into a mixture of (2R)-2-[4'-(2-benzyl-benzo[b]-thiophen-3-yl)-3,5-dibromo-biphenyl-4-yloxy]-4-(I,3-dioxo-1,3-dihydro-isoindol-2-yl)-butyric acid methyl ester (0.5, 0.063 mmol), methyl alcohol (10 mL), and water (0.5 mL). The reaction mixture was stirred at room temperature for 24 hours, poured into water, acidified with HCl (2 N), and extracted with ethyl ether. The organic extracts were dried over $MgSO_4$. Evaporation and purification by flash chromatography on acidic silica gel (hexanes/EtAOc 4:1) gave white solid (0.32 g, 63% yield): mp 95–97° C.; MS m/e 811 (M⁺);

Analysis for: $C_{40}H_{31}Br_2NO_6S$ Calc'd: C, 59.04; H, 3.81; N, 1.72 Found: C, 58.43; H, 4.09; N, 1.59.

EXAMPLE 45

N-{(3R)-3-[4'-(2-benzyl-benzo[b]thiophen-3-yl)-3,5-dibromo-biphenyl-4-yloxy]-3-carboxy-propyl]-phthalamic acid Sodium hydroxide (2 N, 5.0 mL) was added into a mixture of (2R)-2-[4'-(2-benzyl-benzo[b]-thiophen-3-yl)-3,5-dibromo-biphenyl-4-yloxy]-4-(1,3-dioxo-1,3-dihydro-isoindol-2-yl)-butyric acid methyl ester (1.0g, 1.26 mmol), methyl alcohol (10 ml) and tetrahydrofuran (10 mL). The reaction mixture was stirred at room temperature for 1 hour, poured into water, acidified with HCl (2 N), and extracted with ethyl ether. The organic extracts were dried over $MgSO_4$. Evaporation and purification by flash chromatography on acidic silica gel (hexanes/EtAOc 2:1) gave white solid (0.82 g, 74% yield): mp 130–132° C.; MS m/e 797 (M⁺);

Analysis for: $C_{39}H_{29}Br_2NO_6S$ Calc'd: C, 58.59; H, 3.66; N, 1.75 Found: C, 58.20; H, 3.97; N, 1.67.

EXAMPLE 46

(2R)-2-[4-(2-benzyl-benzo[b]thiophene-3-yl)-4''-chloro-[1,1';3', 1'']terphenyl-4-yloxy]-3-phenyl-propionic acid This compound was prepared from 4-(2-benzyl-benzo[b]-thiophen-3-yl)-4''-chloro[1,1;3', 1''-terphenyl]-4'-ol , and (S)-(−)-3-phenyllactic acid methyl ester, in substantially the same manner, as described in Example 1, steps g–h , and was obtained as a white solid, mp 85–87° C.; MS nile 649 (M−H)⁺;

Analysis for: $C_{42}H_{31}ClO_3S \times 1.2 H_2O$ Calc'd: C, 74.97; H, 5.00 Found: C, 74.74; H, 4.84.

EXAMPLE 47

(2S)-2-[4'-(2-benzyl-benzofuran-3-yl)-biphenyl-4-yloxy]-4-phenyl-butyric acid

The title compound was prepared from 4'-(2-benzyl-benzofuran-3-yl)-biphenyl-4-ol, and (R)-(−)-2-hydroxy-4-phenylbutyric acid methyl ester, in substantially the same manner, as described in Example 1, steps g–h , and was obtained as a white solid, mp 152–154° C.; MS m/e 537 (M−H)⁺;

Analysis for: $C_{37}H_{30}O_4$ Calc'd: C, 82.50; H, 5.61 Found: C, 82.26; H, 5.56.

EXAMPLE 48

(2R)-2-[4'-(2-benzyl-benzofuran-3-yl)-biphenyl-4-yloxy]-4-(1,3-dioxo-1,3-dihydro-isoindol-2-yl)-butyric acid The title compound was prepared from 4'-(2-benzyl-benzofuran-3-yl)-biphenyl-4-ol, and (S)-(+)-a-1,3-dioxo-2-isoindolinebutyric acid methyl ester, in substantially the same manner, as described in Example 1 step g, and Example 43 step b, and was obtained as a yellow solid, mp 182–184° C.; MS m/e 606 (M−H)⁺;

Analysis for: $C_{39}H_{29}NO_6$ Calc'd: C, 76.40; H, 4.87 Found: C,76.43; H, 5.00.

EXAMPLE 49

(2S)-2-[4'-(2-benzyl-benzofuran-3-yl)-3,5-dibromo-biphenyl-4-yloxy]-3-henyl-propionic acid The title compound was prepared from 4'-(2-benzyl-benzofuran-3-yl)-3,5-dibromo-biphenyl-4-ol, and (R)-(+)-3-phenyllactic acid methyl ester, in substantially the same manner, as described in Example 1, steps g–h , and was obtained as a white solid, mp 90–92° C.; MS m/e 679 (M−H⁺;

Analysis for: $C_{36}H_{26}Br_2O_4$ Calc'd: C, 63.36; H, 3.84 Found: C, 63.67; H, 3.86.

EXAMPLE 50

(2S)-2-[4'-(2-benzyl-benzofuran-3-yl )-3-bromo-biphenyl-4-yloxy]-3-phenyl-propionic acid The title compound was prepared from 4'-(2-benzyl-benzofuran-3-yl)-3-dibromo-biphenyl-4-ol, and (R)-(+)-3-phenyllactic acid methyl ester, in substantially the same manner, as described in Example 1, steps g–h , and was obtained as a white solid, mp 80–82° C.; MS m/e 601 (M−H)⁺;

Analysis for: $C_{36}H_{27}BrO_4$ Calc'd: C, 71.65; H, 4.51 Found: C, 70.87; H, 4.55.

EXAMPLE 51

(2R)-2-[4'-(2-benzyl-benzofuran-3-yl)-3,5-dibromo-biphenyl-4-yloxy]-4-methyl-pentanoic acid The title compound was prepared from 4'-(2-benzyl-benzofuran-3-yl)-3,5-dibromo-biphenyl-4-ol, and (S)-(−)-hydroxyisocaproic acid methyl ester, in substantially the same manner, as described in Example 1, steps g–h , and was obtained as a white solid, mp 81–83° C.; MS m/e 645 (M−H)⁺;

Analysis for: $C_{33}H_{28}Br_2O_4$ Calc'd: C, 61.13; H, 4.35 Found: C, 61.30; H, 4.06.

EXAMPLE 52

2-[4'-(2-benzyl-benzofuran-3-yl)-3,5-dibromo-biphenyl-4-yloxy]-hexanoic acid

The title compound was prepared from 4'-(2-benzyl-benzofuran-3-yl)-3,5-dibromo-biphenyl-4-ol, and ethyl DL-2-hydroxycaproate, in substantially the same manner, as described in Example 1, steps g–h , and was obtained as a white solid, mp 75–76° C.; MS m/e 645 (M–H)$^+$;

Analysis for: $C_{33}H_{28}$ r$_2O_4$ Calc'd: C, 61.13; H, 4.35 Found: C, 61.27; H, 4.23.

EXAMPLE 53

(2S)-2-[4'-(2-benzyl-benzofuran-3-yl)-3,5-dibromo-biphenyl-4-yloxy]-butyric acid The title compound was prepared from 4'-(2-benzyl-benzofuran-3-yl)-3,5-dibromo-biphenyl-4-ol, and tert-butyl (S)-(–)-hydroxybutyrate, in substantially the same manner, as described in Example 1, steps g–h , and was obtained as a white solid, mp 79–80° C.; MS m/e 617 (M–H)$^+$;

Analysis for: $C_{31}H_{24}Br_2O_4$ Calc'd: C, 60.02; H, 3.90 Found: C, 60.41; H, 3.80.

EXAMPLE 54

(2S )-2-[4'-(2-benzyl-benzofuran-3-yl)-3,5-dibromo-biphenyl-4-yloxy]-octanoic acid The title compound was prepared from 4'-(2-benzyl-benzofuran-3-yl)-3,5-dibromo-biphenyl-4-ol, and tert-butyl (R)-2-hydroxyoctanoate, in substantially the same manner, as described in Example 1, steps g–h , and was obtained as a white solid, mp 72–74° C.; MS m/e 673 (M–H)$^+$;

Analysis for: $C_{35}H_{32}Br_2O_4$ Calc'd: C, 62.15; H, 4.77 Found: C, 62.01; H, 4.71.

EXAMPLE 55

(2S)-2-[4-(2-benzyl-benzofuran-3-yl)-4"-methoxy-[1,1';3',1"]terphenyl-4'-yloxy]-3-phenyl-propionic acid The title compound was prepared from 4-(2-benzyl-benzofuran-3-yl)-4"-methoxy-[1,1';3',1"]terphenyl-4'-ol, and (S)-(–)-3-phenyllactic acid methyl ester, in substantially the same manner, as described in Example 1, steps g–h , and was obtained as a white solid, mp 73–75° C.; MS m/e 629 (M–H)$^+$;

Analysis for: $C_{43}H_{34}O_5 \times 0.5$ H$_2$O Calc'd: C, 80.73; H, 5.51 Found: C, 80.45; H, 5.32.

EXAMPLE 56

[4-(2-benzyl-benzo[b]-thiophen-3-yl)-5'-bromo-3", 4"-dimethoxy[1,1';3',1"-terphenyl]-4'-yloxy]-acetic acid The title compound was prepared from 4-(2-benzyl-benzo[b]thiophene-3-yl)-5-bromo-3",4"-dimethoxy-[1,1';3',1"] terphenyl-4'-ol, and methyl bromoacetate, in substantially the same manner, as described in Example 2, steps g, and was obtained as a white solid, mp 103–105° C.; MS m/e 663 (M–H)$^+$;

Analysis for: $C_{37}H_{29}BrO_5S$ Calc'd: C, 66.77; H, 4.39 Found: C, 66.77; H, 4.30.

EXAMPLE 57

[4-(2-benzyl-benzo[b]-thiophen-3-yl)-5'-bromo-3"-methoxy[1,1';3',1"-terphenyl]-4'-yl)oxy]-acetic acid The title compound was prepared from 4-(2-benzyl-benzo[b]thiophene-3-yl)-5-bromo-3"-methoxy-[1,1';3',1"] terphenyl-4'-ol, and methyl bromoacetate, in substantially the same manner, as described in Example 2, steps g, and was obtained as a white solid, mp 88–90° C.; MS m/e 633 (M–H)$^+$;

Analysis for: $C_{36}H_{27}BrO_4S$ Calc'd: C, 68.03; H, 4.28 Found: C, 66.75; H, 4.18.

EXAMPLE 58

[[3,3-dimethoxy-5-[4-[2-(phenylmethyl)benzyl-benzo[b]-thiophen-3-yl)-[1,1';3',1"-terphenyl]-4'-yl) oxy]-acetic acid The title compound was prepared from 3,3"-dimethoxy-5'-{4-[2-(phenylmethyl)benzo[b]thien-3-yl]phenyl}[1,1';3', 1"-terphenyl]-2'-ol, and methyl bromoacetate, in substantially the same manner, as described in Example 2, steps g, and was obtained as a white solid, mp 83–85° C.; MS m/e 661(M–H)$^+$;

Analysis for: $C_{43}H_{34}O_5S \times 0.8$ H$_2$O Calc'd: C, 76.26; H, 5.30 Found: C, 76.35; H, 5.07.

EXAMPLE 59

[4-(2-benzyl-benzo[b]-thiophen-3-yl)-4"-methoxy[1, 1';3',1"-terphenyl]-4'-yl)oxy]-acetic acid The title compound was prepared from 4-(2-benzyl-benzo[b]thiophene-3-yl)-4"-methoxy-[1,1';3',1"]terphenyl-4'-ol, and methyl bromoacetate, in substantially the same manner, as described in Example 2, steps g , and was obtained as a white solid, mp 75–77° C.; MS m/e 555 (M–H)$^+$;

Analysis for: $C_{36}H_{28}O_4S \times 1$ H$_2$O Calc'd: C, 75.24; H, 5.26 Found: C, 75.56; H, 5.03.

EXAMPLE 60

[4-(2-benzyl-benzo[b]-thiophen-3-yl)-4"-methoxy[1, 1';3',1"-terphenyl]-4'-yl)oxy]-acetic acid The title compound was prepared from 4-(2-benzyl-benzo[b]thiophene-3-yl)-3",4"-dimethoxy-[1,1';3',1"]terphenyl-4'-ol, and methyl bromoacetate, in substantially the same manner, as described in Example 2, steps g, and was obtained as a white solid, mp 95–97° C.; MS m/e 585 (M–H)$^+$;

Analysis for: $C_{37}H_{30}O_5S \times 0.8$ H$_2$O Calc'd: C, 73.93; H, 5.30 Found: C, 73.96; H, 4.98.

EXAMPLE 61

[4-(2-benzyl-benzo[b]-thiophen-3-yl)-3",4",5"-trimethoxy[1,1';3',1"-terphenyl]-4-yl)oxy]-acetic acid The title compound was prepared from 4-(2-benzyl-benzo[b]thiophene-3-yl)-2",3",4"-trimethoxy-[1,1';3',1"] terphenyl-4'-ol, and methyl bromoacetate, in substantially the same manner, as described in Example 2, steps g, and was obtained as a white solid, mp 93–94° C.; MS m/e 615 (M–H)$^+$;

Analysis for: $C_{38}H_{32}O_6S \times 1.0$ H$_2$O Calc'd: C, 71.90; H, 5.40 Found: C, 72.12; H, 5.14.

EXAMPLE 62

[4-(2-benzyl-benzo[b]-thiophen-3-yl)-[1,1';3',1"] terphenyl]-4'-yl)oxy]-acetic acid The title compound was prepared from 4-(2-benzyl-benzo[b]thiophene-3-yl)-[1,1';3',1"]terphenyl-4'-ol, and methyl bromoacetate, in substantially the same manner, as described in Example 2, steps g, and was obtained as a white solid, mp 88–90° C.; MS m/e 525 (M–H)+;

Analysis for: $C_{35}H_{26}O_3S \times 0.3\ H_2O$ Calc'd: C, 79.01; H, 5.04 Found: C, 79.10; H, 4.92.

EXAMPLE 63

4-[4'-(2-benzyl-benzofuran-3-yl)-biphenyl-4-yloxymethyl]-benzoic acid

The title compound was prepared from 4-(2-benzyl-benzo[b]thiophene-3-yl)-4''-methoxy-[1,1';3',1'']terphenyl-4'-ol, and 4'-bromomethyl-benzoic acid methyl aster, in substantially the same manner, as described in Example 2, steps g, and was obtained as a white solid, mp 208–210° C.; MS m/e 509 (M–H)+;

Analysis for: $C_{35}H_{26}O_4$ Calc'd: C, 81.47; H, 5.20 Found: C, 81.41; H, 5.24.

EXAMPLE 64

(2R)-2-[4'-(2-Benzyl-4,5-dimethyl-thiophen-3-yl)-biphenyl-4-yloxy[3-phenyl-propionic acid The title compound was prepared from 4'-(2-benzyl-4,5-dimethyl-thiophen-3-yl)-biphenyl-4-ol, and (S)-(−)-3-phenyllactic acid methyl ester, in substantially the same manner, as described in Example 29, and was obtained as an off-white solid, mp 142–144° C.; MS m/e 517 (M–H)+;

Analysis for: $C_{34}H_{30}O_3S$ Calc'd: C, 78.73; H, 5.83 Found: C, 78.06; H, 5.68.

EXAMPLE 65

(2R)-2-[4'-(2-Benzoyl-benzofuarn-3,5-dimethyl-biphenyl-4-yloxy]-3-phenyl-propionic acid The title compound was prepared from 4'-(2-benzyl-benzofuarn-3-yl)-3,5-dimethyl-biphenyl-4-ol, and (R)-(+)-3-phenyllactic acid methyl ester, in substantially the same manner, as described in Example 1 steps g–h, and was obtained as an off-white solid, mp 68–70° C.; MS m/e 551 (M–H)+;

Analysis for: $C_{38}H_{32}O_4$ Calc'd: C, 82.58; H, 5.84 Found: C, 80.67; H, 5.90.

EXAMPLE 66

(2R)-2-[4'-(2-Benzoyl-benzofuarn-3-yl)-3-nitro-biphenyl-4-yloxy]-3-phenyl-propionic acid The title compound was prepared from 4'-(2-benzoyl-benzofuarn-3-yl)-3-nitro-biphenyl-4-ol, and (S)-(−)-3-phenyllactic acid methyl ester, in substantially the same manner, as described in Example 1 steps g–h, and was obtained as a yellow solid, MS m/e 584 (M–H)+;

Analysis for: $C_{36}H_{25}NO_7 \times 0.5\ H_2O$ Calc'd: C, 72.97; H, 4.42; N, 2.36 Found: C, 72.67; H, 4.25; N, 2.39.

EXAMPLE 67

(2R)-2-{4'-2-(Hydroxy-phenyl-methyl)-benzofuarn-3-yl-3-nitro-biphenyl-4-yloxy]-3-phenyl-propionic acid The title compound was prepared from 4'-[2-(hydroxy-phenyl-methyl)-benzofuarn-3-yl)-3-nitro-biphenyl-4ol, and (S)-(−)-3-phenyllactic acid methyl ester, in substantially the same manner, as described in Example 1 steps g–h, and was obtained as a brown solid, mp 121–125° C.; MS m/e 584 (M–H)+;

Analysis for: $C_{36}H_{27}NO_7 \times 0.75\ H_2O$ Calc'd: C, 72.17; H, 4.79; N, 2.34 Found: C, 72.25; H, 4.80; N, 2.16.

EXAMPLE 68

(2R)-2-[4'-(2Benzyl-benzofuarn-3-yl)-3-nitro-biphenyl-4-yloxy]-3-phenyl-propionic acid Step a) 4'-(2-Benzyl-benzofuarn-3-yl)-3-nitro-biphenyl-4-ol Iron (III) nitrate nonahydrate (8.04 g, 19.9 mmol) was added to a solution of 4'-(2-benzyl-benzofuran-3-yl)-biphenyl-4-ol (6.8 g, 18.1 mmol) in absolute ethanol (80 mL), and the mixture was heated to 45° C. for 1.5 hour. The reaction mixture was cooled to room temperature and poured into HCl (0.1 N) and extracted with ethyl acetate 3 times. The extracts were washed with brine, dried over MgSO$_4$ and concentrated in vacuo. Purification by flash chromatography (10% EtOAc/petroleum ether) gave the title compound as a yellow solid, mp 75° C.; MS m/e 420 (M–H)+.

Analysis for $C_{27}H_{19}NO_4 \cdot 0.5\ H_2O$: Calcd. C, 75.34; H, 4.68; N, 3.25. Found: C, 75.6; H, 4.51; N, 3.11.

Step b) (2R)-2-[4'-(2-Benzyl-benzofuarn-3-yl)-3-nitro-biphenyl-4-yloxy]-3-phenyl-propionic acid This compound was prepared from 4'-(2-benzyl-benzofuarn-3-yl)-3-nitro-biphenyl-4-ol, and (S)-(−)-3-phenyllactic acid methyl ester, in substantially the same manner, as described in Example 1 steps g–h, and was obtained as a light brown solid, mp 77–82° C.; MS m/e 587 (M+);

Analysis for: $C_{36}H_{27}NO_6 \times 1\ H_2O$ Calc'd: C, 73.59; H, 4.97; N, 2.38 Found: C, 73.89; H, 4.99; N, 2.29.

EXAMPLE 69

(2R)-2-[4'-(3-Benzyl-3H-imidazol[4,5-b]pyridin-2-yl)-biphenyl-4-yloxy]-3-phenyl-propionic acid sodium salt Step a) Benzyl-(3-nitro-pyridin-2-yl)-amine To a stirred solution of 2-chloro-3-nitropyridine (10 g, 63.1 mmol) in toluene (100 mL) was added in one portion benzyl amine (13.5 g, 126 mmol) and set to reflux overnight. The reaction was cooled to room temperature and filtered. The solvent was evaporated and the residue was purified by flash chromatography (10% EtOAc/petroleum ether) affording the title compound as a yellow solid, mp 78° C.; MS m/e 229 (M+). Analysis for $C_{12}H_{11}N_3O_2$: Calcd. C, 62.87; H, 4.84; N, 18.33. Found: C, 63.15; H, 4.74; N, 18.28.

Step b) Benzyl-pyridine-2,3-diamine

A solution of benzyl-(3-nitro-pyridin-2-yl)-amine (5.00 g, 21.8 mmol) and tin (II) chloride dihydrate (24.6 g, 109.1 mmol) in EtOAc (100 ml) was refluxed for 2 hours. The reaction was cooled to room temperature, carefully quenched with sat. aq. NaHCO$_3$ (until basic), diluted with EtOAc (350 mL), stirred overnight and filtered. The biphasic filtrate was separated and the aqueous phase extracted with EtOAc. The combined organic extracts were dried (MgSO$_4$) and concentrated. Purification by flash chromatography (40%–50% EtOAc/petroleum ether) gave the title compound as a light red solid, mp 88° C.; MS m/e 200 (M +H)+. Analysis for $C_{12}H_{13}N_3$: Calcd. C, 72.33; H, 6.58; N, 21.09. Found: C, 72.23; H, 6.68; N, 21.42.

Step c) 3-Benzyl-1,3-dihydro-imadazo[4,5-b]pyridin-2-one

Ethyl chloroformate (3.34 g, 30.7 mmol) was added to a solution of benzyl-pyridine-2,3-diamine (2.78 g, 14.0 mmol) in chloroform (70 mL), and the mixture was refluxed for 1.5 hours. The reaction mixture was washed with aqueous NaHCO$_3$ and water, and evaporated to dryness. The residue was subjected to to column chromatography on silica gel. Elution with 50% EtOAc/chloroform gave a brown oil (a mixture of mono and bis ethoxycarbonylated compounds. A solution of this oil in absolute ethanol (15 mL) was added to a solution of sodium ethoxide (10 mmol) in absolute ethanol (15 mL), and the mixture was refluxed for 3 hours. The reaction mixture was concentrated in vacuo. The residue was diluted with water, neutralized with 2 N HCl and extracted with ethyl acetate. The extract was washed with water, dried over MgSO$_4$, and concentrated. Purification by flash chromatography (20%–40% EtOAc/petroleum ether) gave the title compound as an orange solid, mp 172° C.; MS m/e 225 (M$^+$). Analysis for C$_{13}$H$_2$N$_3$0: Calcd. C, 69.32; H, 4.92; N, 18.65. Found: C, 69.08; H, 5.01; N, 18.00.

Step d) 3-Benzyl-2-(4'-methoxy-biphenyl-4-yl)-3H-imadazo[4,5-b]pyridine

Phosphorus pentachloride (0.92 g, 4.44 mmol) was added to a refluxing suspension of 3-benzyl-1,3-dihydro-imadazo [4,5-b]pyridin-2-one (1.0 g, 4.44 mmol) in phosporus oxychloride (15 mL). The mixture was refluxed for 12 hours. The solvent was then removed under reduced pressure. The residue was treated with water and basified with sodium hydroxide (5 N) with external cooling. The solution was extracted with ethyl acetate and washed with brine and dried over MgSO$_4$ and concentrated. The residue was purified by flash chromatography (20%–30% EtOAc/petroleum ether) and used in the following step.

Step e)

The above haloimidazopyridine (0.423 g, 1.74 mmol) and tetrakis(triphenylphosphine)palladium(0) (100 mg, 0.09 mmol) were dissolved in the minimum amount of 1,2-dimethoxyethane and stirred for 10 minutes at room temperature under a nitrogen atmosphere. 4'-Methoxy-biphenyl-4-boronic acid (0.61 g, 1.91 mmol) was added, followed by aqueous sodium carbonate (2 M, 3.5 mL). The mixture was refluxed for 12 hours, diluted with water and extracted with methylenechloride and dried over MgSO$_4$ and concentrated. Purification by flash chromatography (5%–10% EtOAc/methylenechloride) gave the title compound as a white solid, mp 159° C.; MS m/e 391 (M$^+$). Analysis for C$_{26}$H$_2$,N$_3$0 Calcd.: C, 79.77; H, 5.41; N, 10.73. Found: C, 79.48; H, 5.50; N, 10.80.

Step f) (2R)-2-[4'-(3-Benzyl-3H-imidazol[4,5-b]pyridin-2-yl)-biphenyl-4-yloxy]-3-phenyl-propionic acid sodium salt The title compound was prepared from 3-benzyl-2-(4'-methoxy-biphenyl-4-yl)-3H-imadazo[4,5-b]pyridine and (S)-(–)-3-phenyllactic acid methyl ester, in substantially the same manner, as described in Example 1 steps d and g–h, and was obtained as a white solid, MS m/e 524 (M–H)$^+$;

Analysis for: C$_{34}$H$_{27}$N$_3$O$_3$Na Calc'd: C, 72.20; H, 5.15; N, 7.43 Found: C, 72.59; H, 5.02; N, 7.38.

EXAMPLE 70

(2S)-2-[4'-(1-Benzyl-1H-benzimidazol-2-yl)-biphenyl-4-yloxy]-3-phenyl-propionic acid Step a) 3-Benzyl-2-(4'-methoxy-biphenyl-4-yl)-1H-benzimidazole This compound was prepared from 3-benzyl-2-chloro-1 H-benzimidazole and 4-methoxy-biphenyl-4'-boronic acid, in substantially the same manner, as described in Example 69 step e , and was obtained as a white solid, mp 208° C.; MS m/e 391 (M+H)$^+$.

Step b) (2S)-2-[4'-(1-Benzyl-lH-benzimidazol-2-yl)-biphenyl-4-yloxy]-3-phenyl-propionic acid This compound was prepared from 1-benzyl-2-(4'-methoxy-biphenyl-4-yl)-3H-imadazo[4,5-b]pyridine and (S)-(–)-3-phenyllactic acid methyl ester, in substantially the same manner, as described in Example 1 steps d and g–h, and was obtained as a light yellow solid, mp 254° C.; MS m/e 523 (M–H)$^+$;

Analysis for: C$_{35}$H$_{28}$N$_2$O$_3$×0.6 H$_2$O Calc'd: C, 78.52; H, 5.45; N, 5.24 Found: C, 78.01; H, 5.38; N, 5.15.

EXAMPLE 71

(2S)-2-[4'-(5-acetyl-thiophen-2-yl)-biphenyl-4-yloxy]-3-phenyl-propionic acid sodium salt The title compound was prepared from 4'-(5-acetyl-thiophen-2-yl)-biphenyl-4-ol and (R)-(+)-3-phenyllactic acid methyl ester, in substantially the same manner, as described in Example 1 steps d and g–h, and was obtained as a yellow solid, MS m/e 443 (M+H)$^+$;

Analysis for: C$_{27}$H$_{22}$O$_4$SNa Calc'd: C, 69.14; H, 4.62 Found: C, 69.09; H, 4.78

The following compounds were prepared in substantially the same manner as described in Examples 1–71

2-bromo-3-(4'-methoxy-biphenyl-4-yl)-benzofuran
4'-(2-bromo-benzofuran-3-yl)-biphenyl-4-ol
2-butyl-3-(4'-methoxy-biphenyl-4-yl)-benzofuran
1-[3-(4'-methoxy-biphenyl-4-yl)-benzofuran-2-yl]-butan-1-one
[3-(4'-hydroxy-biphenyl-4-yl)-benzofuran-3-yl]-phenyl-methanone
4'-benzo[b]thiophen-3-yl-biphenyl-4-ol
3-(4'-methoxy-biphenyl-4-yl)-benzo[b]thiophene
4'-(2-butyl-benzo[b]thiophen-3-yl)-biphenyl-4-ol
4'-(2-benzyl-benzo[b]thiopen-3-yl)-biphenyl-4-ol
[3-(4'-hydroxy-biphenyl-4-yl)-benzo[b]thiophen-2-yl]-phenyl-methanone
(4-fluoro-phenyl)-[3-(4'-methoxy-biphenyl-4-yl)-benzo[b]thiophen-2-yl]-methanol
2-(4-fluoro-benzyl)-3-(4'-methoxy-biphenyl-4-yl)-benzo[b]thiophene
4'-{2-hydroxy-(4-methoxy-phenyl)-methyl]-benzo[b]thiophen-3-yl }-biphenyl-4-ol
1-[3-(4'-hydroxy-biphenyl-4-yl)-benzofuran-2-yl]-ethanone
4'-[2-(4-methoxy-benzyl)-benzo[b]thiophen-3-yl]-biphenyl-4-ol
4'-(2-ethyl-benzofuran-3-yl)-biphenyl-4-ol
2-[4'-(2-benzyl-benzofuran-3-yl)-biphenyl-4-yloxy]-propionic acid ethyl ester
4'-[2-(3,4-dimethoxy-benzyl)-benzothiophen-3-yl]-biphenyl-4-ol
4'-[2-(2,4-dimethoxy-benzyl)-benzothiophen-3-yl]-biphenyl-4-ol
3-(4'-methoxy-biphenyl-4-yl)-thiophen-2-carboxaldehyde
4-[3-(4'-hydroxy-biphenyl-4-yl)-benzo[b]thiophen-2-ylmethyl]-benzene-1,2-diol
4'-[2-(2,2-dimethyl-benzo[1,3]dioxo-5-ylmethyl)-benzothiophen-3-yl]-biphenyl-4-ol
[3-(4-methoxy-biphenyl-4-yl)-thiophen-2-yl]-phenyl-methanol
2-benzyl-3-(4'-methoxy-biphenyl-4-yl)-thiophene
4'-(2-thiazole-2-ylmethyl-benzo[b]thiophen-3-yl)-biphenyl-4-ol
4'-[2-(4-hydroxy-benzyl)-benzo[b]thiophen-3-yl]-biphenyl-4-ol
2-benzyl-3-(4'-methoxy-biphenyl-4-yl)-furo[2,3-b]pyridine
4'-(2-benzyl-furo[2,3-b]pyridin-3-yl)-biphenyl-4-ol 4,4"-dimethoxy-5'-{4-[2-(phenylmethyl)benzo[b]thiophen-3-yl]phenyl}[1,1';3',1"-terphenyl]-2'-ol
4-(2-benzyl-benzo[b]thiophen-3-yl)-5'-bromo-4"-methoxy-[1,1';3',1"]terphenyl-
4'-(2-benzyl-benzo[b]thiophen-3-yl)-3,5-diiodo-biphenyl-4-ol 4'-(2-benzyl-benzofuran-3-yl)-3,5-dibromo-biphenyl-4-ol
4'-(2-benzyl-benzofuran-3-yl)-3-bromo-biphenyl-4-ol

What is claimed is:

1. A compound of formula I having the structure

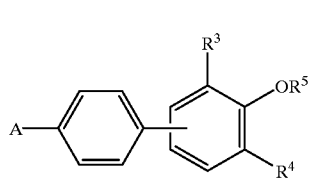

wherein

A is

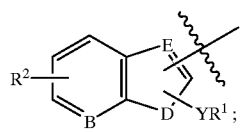

B is carbon;
D is oxygen, sulfur, or nitrogen;
E is carbon;
Y is a bond, methylene, C(O), or CH(OH);
$R^1$ is alkyl having 1 to 12 carbons, aryl of 6–12 carbon atoms, arylalkyl of 7–15 carbon atoms, halogen, carboxaldehyde, trifluoromethyl, alkoxy of 1–6 carbon atoms, 2,2-dimethyl-1,3-benzodioxole, Het-alkyl wherein the alkyl moiety have 1–6 carbon atoms, or aryl of 6–10 carbon atoms which is mono-, di-, or tri-substituted with halogen, trifluormethyl, or alkoxy of 1–6 carbon atoms;

Het is

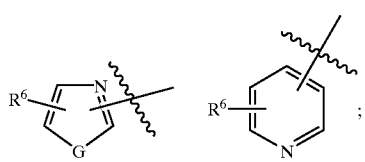

G is oxygen, sulfur or nitrogen;
$R^2$ and $R^{2a}$ are each, independently, hydrogen, alkyl of 1–6 carbon atoms, alkoxy of 1–6 carbon atoms, halogen, trifluoromethyl;
$R^3$ and $R^4$ are each, independently, hydrogen, halogen, alkyl of 1–6 carbon atoms, aryl of 6–10 carbon atoms, trifluoromethyl, alkoxy of 1–6 carbon atoms, nitro, amino, carboalkoxy, carbamide, carbamate, urea, alkylsulfoamide, arylsulfoamide, cycloalkyl of 3–8 carbon atoms, —$NR^7(CH_2)_mCO_2H$, pyrrolidinone, a heterocycic ring having 5 to 7 atoms and having 1 to 3 heteroatoms selected from oxygen, nitrogen, or sulfur, or aryl of 6–10 carbon atoms mono-, di-, or tri-substituted with trifluoromethyl, alkyl of 1–6 carbon atoms or, alkoxy of 1–6 carbon atoms;
$R^5$ is hydrogen, alkyl of 1–6 carbon atoms, —$CH(R^8)R^9$, —$C(CH_2)_nCO_2R^{10}$, —$C(CH_3)_2CO_2R^{10}$, —$CH(R^8)(CH_2)_nCO_2R^{10}$, —$CH(R^8)C_6H_4CO_2R^{10}$
$R^6$ is alkylene of 1 to 3 carbon atoms
$R^7$ is hydrogen or alkyl of 1 to 6 carbon atoms,
$R^8$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety has 1–6 carbon atoms;

Q is

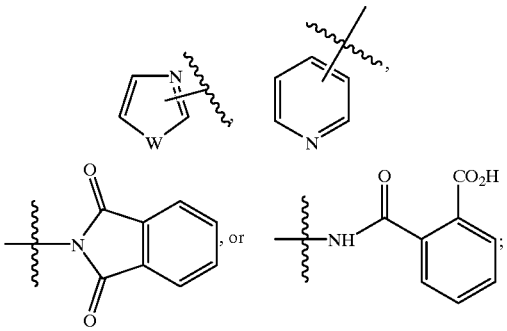

W is oxygen, sulfur, or nitrogen;
$R^9$ is —$CO_2R^{12}$, —$CONHR^{12}$, tetrazole, —$PO_3R^{12}$;
$R^{10}$ is hydrogen, alkyl of 1–6 carbon atoms, aryl of 7–15 carbon atoms, or aralkyl of 7–15 carbon atoms;
$R^{12}$ is hydrogen, alkyl, aryl of 6–12 carbon atoms, aralkyl of 7–15 carbon atoms;
m=1–3;
n=1–6;
with the proviso that when $R^1$ is halogen, Y is a bond;
or a pharmaceutically acceptable salt thereof.

2. The compound according to claim 1, wherein
A is

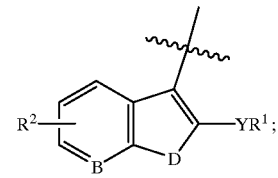

wherein
D is oxygen or sulfur;
or a pharmaceutically acceptable salt thereof.

3. The compound according to claim 1 which is (4'-benzofuran-3-yl-biphenyl-4-yloxy)-acetic acid or a pharmaceutically acceptable salt thereof.

4. The compound according to claim 1 which is 2-(4'-benzofuran-3-yl-biphenyl-4-yloxy)-3-phenyl-propionic acid or a pharmaceutically acceptable salt thereof.

5. The compound according to claim 1 which is [4'-(2-bromo-benzofuran-3-yl)-biphenyl-4-yloxy]-acetic acid or a pharmaceutically acceptable salt thereof.

6. The compound according to claim 1 which is 2-[4'-(2-bromo-benzofuran-3-yl)-biphenyl-4-yloxy]-3-phenyl-propionic acid or a pharmaceutically acceptable salt thereof.

7. The compound according to claim 1 which is 4'-(2-butyl-benzofuran-3-yl)-biphenyl-4-ol or a pharmaceutically acceptable salt thereof.

8. The compound according to claim 1 which is [4'-(2-butyl-benzofuran-3-yl)-biphenyl-4-yloxy]-acetic acid or a pharmaceutically acceptable salt thereof.

9. The compound according to claim 1 which is 2-[4'-(2-butyl-benzofuran-3-yl)-biphenyl-4-yloxy]-3-phenyl-propionic acid or a pharmaceutically acceptable salt thereof.

10. The compound according to claim 1 which is 2-[4'-(2-benzyl-benzofuran-3-yl)-biphenyl-4-yloxy]-3-phenyl-propionic acid or a pharmaceutically acceptable salt thereof.

11. The compound according to claim 1 which is 2-[4'-(2-butyl-benzo[b]thiophene-3-yl)-biphenyl-4-yloxy]-3-phenyl-propionic acid or a pharmaceutically acceptable salt thereof.

12. The compound according to claim 1 which is 2-[4'-(2-benzyl-benzo[b]thiophene-3-yl)-biphenyl-4-yloxy]-3-phenyl-propionic acid or a pharmaceutically acceptable salt thereof.

13. The compound according to claim 1 which is 2-[4'-(2-benzoyl-benzofuran-3-yl)-biphenyl-4-yloxy]-3-phenyl-propionic acid or a pharmaceutically acceptable salt thereof.

14. The compound according to claim 1 which is (2R)-2-[4'-( 2-benzyl-benzofuran-3-yl)-biphenyl-4-yloxy]-3-phenyl-propionic acid or a pharmaceutically acceptable salt thereof.

15. The compound according to claim 1 which is (2S)-2-[4'-(2-benzyl-benzofuran-3-yl)-biphenyl-4-yloxy]-3-phenyl-propionic acid or a pharmaceutically acceptable salt thereof.

16. The compound according to claim 1 which is (2S)-2-[4'-(2-benzyl-benzofuran-3-yl)-biphenyl-4-yloxy]-3-phenyl-propionic acid tromethamine salt.

17. The compound according to claim 1 which is (2R)-2-[4'-(2-benzyl-benzofuran-3-yl)-biphenyl-4-yloxy]-propionic acid or a pharmaceutically acceptable salt thereof.

18. The compound according to claim 1 which is (R)-[4'-(2-benzyl-benzofuran-3-yl)-biphenyl-4-yloxy]-phenyl-acetic acid or a pharmaceutically acceptable salt thereof.

19. The compound according to claim 1 which is (2R)-2-{4'-[2-(4-fluoro-benzyl-benzo[b]thiophene-3-yl)-biphenyl-4-yloxy]-3-phenyl-propionic acid or a pharmaceutically acceptable salt thereof.

20. The compound according to claim 1 which is (2R)-2-{4'-[2-(4-methoxy-benzyl-benzo[b]thiophene-3-yl)-biphenyl-4-yloxy]-3-phenyl-propionic acid or a pharmaceutically acceptable salt thereof.

21. The compound according to claim 1 which is [4'-(2-butyl-benzo[b]thiophene-3-yl)-biphenyl-4-yloxy]-phenyl-acetic acid or a pharmaceutically acceptable salt thereof.

22. The compound according to claim 1 which is (2R)-2-{4'-[2-(hydroxy-phenyl-methyl)-benzofuran-3-yl)-biphenyl-4-yloxy]-3-phenyl-propionic acid or a pharmaceutically acceptable salt thereof.

23. The compound according to claim 1 which is (2S)-2-[4'-(2-benzyl-benzofuran-3-yl)-biphenyl-4-yloxy]-3-phenyl-propionic acid methyl ester.

24. The compound according to claim 1 which is 2-[4'-(2-benzyl-benzofuran-3-yl)-biphenyl-4-yloxy]-2-methyl-3-phenyl-propionic acid or a pharmaceutically acceptable salt thereof.

25. The compound according to claim 1 which is (2R)-2-{4'-[2-(3,4-dimethoxy-benzyl)-benzo[b]thiophene-3-yl)-biphenyl-4-yloxy]-3-phenyl-propionic acid or a pharmaceutically acceptable salt thereof.

26. The compound according to claim 1 which is (2R)-2-{4'-[2-(2,4-dimethoxy-benzyl)-benzo[b]thiophene-3-yl)-biphenyl-4-yloxy]-3-phenyl-propionic acid or a pharmaceutically acceptable salt thereof.

27. The compound according to claim 1 which is (2R) 2-{4'-[2-(2,2-dimethyl-benzo[1,3]dioxo-5-ylmethyl)-benzo[b]thiophene -3-yl)-biphenyl-4-yloxy]-3-phenyl-propionic acid or a pharmaceutically acceptable salt thereof.

28. The compound according to claim 1 which is (2R)-2-{4'-[2-(3,4-dihydroxy-benzyl)-benzo[b]thiophene-3-yl)-biphenyl-4-yloxy]-3-phenyl-propionic acid or a pharmaceutically acceptable salt thereof.

29. The compound according to claim 1 which is 3-phenyl-2-[4'-(2-thiazole-2-ylmethyl-benzo[b]thiophene-3-yl)-biphenyl-4-yloxy]-propionic acid or a pharmaceutically acceptable salt thereof.

30. The compound according to claim 1 which is (2R)-3-phenyl-2-[4'-(2-pyridin-2-ylmethyl-benzo[b]thiophene-3-yl)-biphenyl-4-yloxy]-propionic acid sodium salt.

31. The compound according to claim 1 which is (2R)-3-phenyl-2-[4'-(2-pyridin-2-ylmethyl-benzo[b]thiophene-3-yl)-biphenyl-4-yloxy]-propionic acid or a pharmaceutically acceptable salt thereof.

32. The compound according to claim 1 which is 4'-(2-benzyl-benzo[b]thiophene-3-yl)-3-bromo-biphenyl-4-ol or a pharmaceutically acceptable salt thereof.

33. The compound according to claim 1 which is 4'-(2-benzyl-benzo[b]thiophene-3-yl)-3,5-dibromo-biphenyl-4-ol or a pharmaceutically acceptable salt thereof.

34. The compound according to claim 1 which is (2R)-2-[4'-(2-benzyl-benzo[b]thiophene-3-yl)-3-bromo-biphenyl-4-yloxy]-3-phenyl-propionic acid or a pharmaceutically acceptable salt thereof.

35. The compound according to claim 1 which is (2R)-2-[4'-(2-benzyl-benzo[b]thiophene-3-yl)-3,5-dibromo-biphenyl-4-yloxy]-3-phenyl-propionic acid or a pharmaceutically acceptable salt thereof.

36. The compound according to claim 1 which is (2R)-2-[4-(2-benzyl-benzo[b]thiophene-3-yl)-4''-methoxy-[1,1';3',1'']terphenyl-4'-yloxy]-3-phenyl-propionic acid or a pharmaceutically acceptable salt thereof.

37. The compound according to claim 1 which is [(4,4''-dimethoxy-5'-{2-(phenylmethyl)benzo[b]thien-3-yl]phenyl)}[1,1';3',1'']-terphenyl]-2'-yl)oxy]-acetic acid or a pharmaceutically acceptable salt thereof.

38. The compound according to claim 1 which is [4-(2-benzyl-benzo[b]-thiophen-3-yl)-5'-bromo-4-methoxy[1,1';3',1''-terphenyl]-4'-yl)oxy]-acetic acid or a pharmaceutically acceptable salt thereof.

39. The compound according to claim 1 which is [4'-(2-benzyl-benzo[b]thiophene-3-yl)-3,5-dibromo-biphenyl-4-yloxy]-acetic acid or a pharmaceutically acceptable salt thereof.

40. The compound according to claim 1 which is [4'-(2-benzyl-benzo[b]thiophene-3-yl)-3-bromo-biphenyl-4-yloxy]-acetic acid or a pharmaceutically acceptable salt thereof.

41. The compound according to claim 1 which is (2S)-[4'-(2-benzyl-benzo[b]thiophene-3-yl)-3,5-dibromo-biphenyl-4-yloxy]-4-phenyl-butyric acid or a pharmaceutically acceptable salt thereof.

42. The compound according to claim 1 which is 4-[4'-(2-benzyl-benzo[b]thiophene-3-yl)-3-bromo-biphenyl-4-yloxy]-butyric acid or a pharmaceutically acceptable salt thereof.

43. The compound according to claim 1 which is N-{(3R)-3-[4'-(2-benzyl-benzo[b]thiophen-3-yl)-3,5-dibromo-biphenyl-4-yloxy]-3-carboxy-propyl]-phthalamic acid or a pharmaceutically acceptable salt thereof.

44. The compound according to claim 1 which is N-{(3R)-3-[4'-(2-benzyl-benzo[b]thiophen-3-yl)-3,5-dibromo-biphenyl-4-yloxy]-3-methoxycarbonyl-propyl]-phthalamic acid or a pharmaceutically acceptable salt thereof.

45. The compound according to claim 1 which is (2R)-2-[4-(2-benzyl-benzo[b]thiophene-3-yl)-4-chloro-[1,1';3',1'']-terphenyl-4'-yloxy]-3-phenyl-propionic acid or a pharmaceutically acceptable salt thereof.

46. The compound according to claim 1 which is (2S)-2-[4'-(2-benzyl-benzofuran-3-yl)-biphenyl-4-yloxy]-4-phenyl-butyric acid or a pharmaceutically acceptable salt thereof.

47. The compound according to claim 1 which is (2R)-2-[4'-(2-benzyl-benzo[b]-thiophen-3-yl)-3,5-dibromo-biphenyl-4-yloxy]-4-(1,3-dioxo-1,3-dihydro-isoindol-2-yl)-butyric acid or a pharmaceutically acceptable salt thereof.

48. The compound according to claim 1 which is (2R)-2-[4'-(2-benzyl-benzofuran-3-yl)-biphenyl-4-yloxy]-4-(1,3-dioxo-1,3-dihydro-isoindol-2-yl)-butyric acid or a pharmaceutically acceptable salt thereof.

49. The compound according to claim 1 which is (2S)-2-[4'-(2-benzyl-benzofuran-3-yl)-3,5-dibromo-biphenyl-4-yloxy]-3-phenyl-propionic acid or a pharmaceutically acceptable salt thereof.

50. The compound according to claim 1 which is (2S)-2-[4'-(2-benzyl-benzofuran-3-yl)-3-bromo-biphenyl-4-yloxy]-3-phenyl-propionic acid or a pharmaceutically acceptable salt thereof.

51. The compound according to claim 1 which is (2R)-2-[4'-(2-benzyl-benzofuran-3-yl)-3,5-dibromo-biphenyl-4-yloxy]-4-methyl-pentanoic acid or a pharmaceutically acceptable salt thereof.

52. The compound according to claim 1 which is 2-[4'-(2-benzyl-benzofuran-3-yl)-3,5-dibromo-biphenyl-4-yloxy]-hexanoic acid or a pharmaceutically acceptable salt thereof.

53. The compound according to claim 1 which is (2S)-2-[4'-(2-benzyl-benzofuran-3-yl)-3,5-dibromo-biphenyl-4-yloxy]-butyric acid or a pharmaceutically acceptable salt thereof.

54. The compound according to claim 1 which is (2S)-2-[4'-(2-benzyl-benzofuran-3-yl)-3,5-dibromo-biphenyl-4-yloxy]-octanoic acid or a pharmaceutically acceptable salt thereof.

55. The compound according to claim 1 which is (2S)-2-[4-(2-benzyl-benzofuran-3-yl)-4"-methoxy-[1,1';3',1"]terphenyl-4'-yloxy]-3-phenyl-propionic acid or a pharmaceutically acceptable salt thereof.

56. The compound according to claim 1 which is [4-(2-benzyl-benzo[b]-thiophen-3-yl)-5'-bromo-3",4"-dimethoxy[1,1';3',1"-terphenyl]-4'-yl)oxy]-acetic acid or a pharmaceutically acceptable salt thereof.

57. The compound according to claim 1 which is [4-(2-benzyl-benzo[b]-thiophen-3-yl)-5'-bromo-3"-methoxy[1,1';3',1"-terphenyl]-4'-yl)oxy]-acetic acid or a pharmaceutically acceptable salt thereof.

58. The compound according to claim 1 which is [[3,3-dimethoxy-5-[4-[2-(phenylmethyl)benzyl-benzo[b]-thiophen-3-yl)-[1,1';3',1"-terphenyl]-4'-yl)oxy]-acetic acid or a pharmaceutically acceptable salt thereof.

59. The compound according to claim 1 which is [4-(2-benzyl-benzo[b]-thiophen-3-yl)-4"-methoxy[1,1';3',1"-terphenyl]-4'-yl)oxy]-acetic acid or a pharmaceutically acceptable salt thereof.

60. The compound according to claim 1 which is [4-(2-benzyl-benzo[b]-thiophen-3-yl)-3",4"-dimethoxy[1,1';3',1"-terphenyl]-4'-yl)oxy]-acetic acid or a pharmaceutically acceptable salt thereof.

61. The compound according to claim 1 which is [4-(2-benzyl-benzo[b]-thiophen-3-yl)-3",4",5"-trimethoxy[1,1';3',1"-terphenyl]-4'-yl)oxy]-acetic acid or a pharmaceutically acceptable salt thereof.

62. The compound according to claim 1 which is [4-(2-benzyl-benzo[b]-thiophen-3-yl)-[1,1';3',1"-terphenyl]-4'-yl)oxy]-acetic acid or a pharmaceutically acceptable salt thereof.

63. The compound according to claim 1 which is 4-[4'-(2-benzyl-benzofuran-3-yl)-biphenyl-4-yloxymethyl]-benzoic acid or a pharmaceutically acceptable salt thereof.

64. The compound according to claim 1 which is (2R)-2-[4'-(2-benzoyl-benzofuarn-3-yl)-3-nitro-biphenyl-4-yloxy]-3-phenyl-propionic acid or a pharmaceutically acceptable salt thereof.

65. The compound according to claim 1 which is (2R)-2-[4'-(2-benzyl-benzofuarn-3-yl)-3-nitro-biphenyl-4-yloxy]-3-phenyl-propionic acid or a pharmaceutically acceptable salt thereof.

66. The compound according to claim 1 which is (2R)-2-{4'-[2-(hydroxy-phenyl-methyl)-benzofuarn-3-yl)-3-nitro-biphenyl-4-yloxy]-3-phenyl-propionic acid or a pharmaceutically acceptable salt thereof.

67. The compound according to claim 1 which is (2S)-2-[4'-(2-benzyl-benzofuarn-3-yl)-3,5-dimethyl-biphenyl-4-yloxy]-3-phenyl-propionic acid or a pharmaceutically acceptable salt thereof.

68. A method of treating metabolic disorders mediated by insulin resistance or hyperglycemia in a mammal in need thereof which comprises administering to said mammal, a compound of formula I having the structure

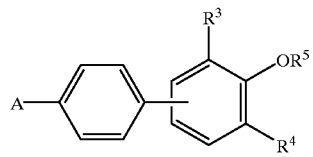

I wherein

A is

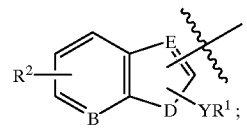

B is carbon;
D is oxygen, sulfur, or nitrogen;
E is carbon or nitrogen;
Y is a bond, methylene, C(O), or CH(OH);
$R^1$ is alkyl having 1 to 12 carbons, aryl of 6–12 carbon atoms, arylalkyl of 7–15 carbon atoms, halogen, carboxaldehyde, trifluoromethyl, alkoxy of 1–6 carbon atoms, 2,2-dimethyl-1,3-benzodioxole, Het-alkyl wherein the alkyl moiety have 1–6 carbon atoms, or aryl of 6–10 carbon atoms which is mono-, di-, or tri-substituted with halogen, trifluormethyl, or alkoxy of 1–6 carbon atoms;

Het is

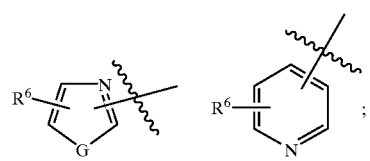

G is oxygen, sulfur or nitrogen;
$R^2$ and $R^{2a}$ are each, independently, hydrogen, alkyl of 1–6 carbon atoms, alkoxy of 1–6 carbon atoms, halogen, trifluoromethyl;

$R^3$ and $R^4$ are each, independently, hydrogen, halogen, alkyl of 1–6 carbon atoms, aryl of 6–10 carbon atoms, trifluoromethyl, alkoxy of 1–6 carbon atoms, nitro, amino, carboalkoxy, carbamide, carbamate, urea, alkylsulfoamide, arylsulfoamide, cycloalkyl of 3–8 carbon atoms, —NR$^7$(CH$_2$)$_m$CO$_2$H, pyrrolidinone, a heterocycic ring having 5 to 7 atoms and having 1 to 3 heteroatoms selected from oxygen, nitrogen, or sulfur, or aryl of 6–10carbon atoms mono-, di-, or tri-substituted with trifluoromethyl, alkyl of 1–6 carbon atoms or, alkoxy of 1–6 carbon atoms;

$R^5$ is hydrogen, alkyl of 1–6 carbon atoms, —CH(R$^8$)R$^9$, —C(CH$_2$)$_n$CO$_2$R$^{10}$, —C(CH$_3$)$_2$R$^{10}$, —CH(R$^8$)(CH$_2$)$_n$CO$_2$R$^{10}$, —CH(R$^8$)C$_6$H$_4$CO$_2$R$^{10}$ $R^6$ is alkylene of 1 to 3 carbon atoms $R^7$ is hydrogen or alkyl of 1 to 6 carbon atoms, $R^8$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety has 1–6 carbon atoms;

Q is

W is oxygen, sulfur, or nitrogen;

$R^9$ is —CO$_2$R$^{12}$, —CONHR$^{12}$, tetrazole, —PO$_3$R$^{12}$;

$R^{10}$ is hydrogen, alkyl of 1–6 carbon atoms, aryl of 7–15 carbon atoms, or aralkyl of 7–15 carbon atoms;

$R^{12}$ is hydrogen, alkyl, aryl of 6–12 carbon atoms, aralkyl of 7–15 carbon atoms;

m=1–3;

n=1–6;

with the proviso that when $R^1$ is halogen, Y is a bond;

or a pharmaceutically acceptable salt thereof.

69. A method of treating or inhibiting type II diabetes in a mammal in need thereof which comprises administering to said mammal, a compound of formula I having the structure

I wherein

A is

B is carbon;

D is oxygen, sulfur, or nitrogen;

E is carbon or nitrogen;

Y is a bond, methylene, C(O), or CH(OH);

$R^1$ is alkyl having 1 to 12 carbons, aryl of 6–12 carbon atoms, arylalkyl of 7–15 carbon atoms, halogen, carboxaldehyde, trifluoromethyl, alkoxy of 1–6 carbon atoms, 2,2-dimethyl-1,3-benzodioxole, Het-alkyl wherein the alkyl moiety have 1–6 carbon atoms, or aryl of 6–10 carbon atoms which is mono-, di-, or tri-substituted with halogen, trifluormethyl, or alkoxy of 1–6 carbon atoms;

Het is

G is oxygen, sulfur or nitrogen;

$R^2$ and $R^{2a}$ are each, independently, hydrogen, alkyl of 1–6 carbon atoms, alkoxy of 1–6 carbon atoms, halogen, trifluoromethyl;

$R^3$ and $R^4$ are each, independently, hydrogen, halogen, alkyl of 1–6 carbon atoms, aryl of 6–10 carbon atoms, trifluoromethyl, alkoxy of 1–6 carbon atoms, nitro, amino, carboalkoxy, carbamide, carbamate, urea, alkylsulfoamide, arylsulfoamide, cycloalkyl of 3–8 carbon atoms, —NR$^7$(CH$_2$)$_m$—CO$_2$H, pyrrolidinone, a heterocycic rind having 5 to 7 atoms and having 1 to 3 heteroatoms selected from oxygen, nitrogen, or sulfur, or aryl of 6–10 carbon atoms mono-, di-, or tri-substituted with trifluoromethyl, alkyl of 1–6 carbon atoms or, alkoxy of 1–6 carbon atoms, $R^5$ is hydrogen, alkyl of 1–6 carbon atoms, —CH(R$^8$)R$^9$, —C(CH$_2$)$_n$CO$_2$R$^{10}$, —C(CH$_3$)$_2$CO$_2$R$^{10}$, —CH(R$^8$)(CH$_2$)$_n$CO$_2$R$^{10}$, —CH(R$^8$)C$_6$H$_4$CO$_2$R$^{10}$ $R^6$ is alkylene of 1 to 3 carbon atoms, $R^7$ is hydrogen or alkyl of 1 to 6 carbon atoms, $R^8$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety has 1–6 carbon atoms;

Q is

-continued

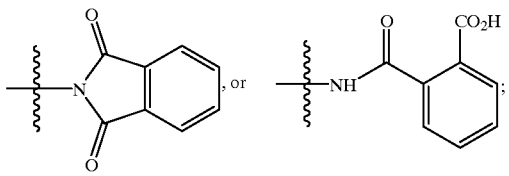

W is oxygen, sulfur, or nitrogen;
$R^9$ is —$CO_2R^{12}$, —$CONHR^{12}$, tetrazole, —$PO_3R^{12}$;
$R^{10}$ is hydrogen, alkyl of 1–6 carbon atoms, aryl of 7–15 carbon atoms, or aralkyl of 7–15 carbon atoms;
$R^{12}$ is hydrogen, alkyl, aryl of 6–12 carbon atoms, aralkyl of 7–15 carbon atoms;
m=1–3;
n 1–6;
with the proviso that when $R^1$ is halogen, Y is a bond;
or a pharmaceutically acceptable salt thereof.

70. A method of modulating glucose levels in a mammal in need thereof which comprises administering to said mammal, a compound of formula I having the structure

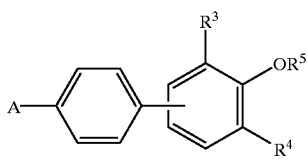

I wherein
A is

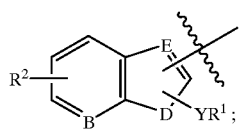

B is carbon;
D is oxygen, sulfur, or nitrogen;
E is carbon or nitrogen;
Y is a bond, methylene, C(O), or CH(OH);
$R^1$ is alkyl having 1 to 12 carbons, aryl of 6–12 carbon atoms, arylalkyl of 7–15 carbon atoms, halogen, carboxaldehyde, trifluoromethyl, alkoxy of 1–6 carbon atoms, 2,2-dimethyl-1,3-benzodioxole, Het-alkyl wherein the alkyl moiety have 1–6 carbon atoms, or aryl of 6–10 carbon atoms which is mono-, di-, or tri-substituted with halogen, trifluormethyl, or alkoxy of 1–6 carbon atoms;
Het is

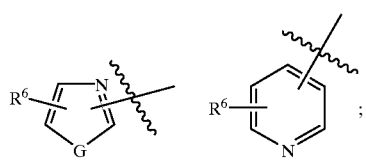

G is oxygen, sulfur or nitrogen;
$R^2$ and $R^{2a}$ are each, independently, hydrogen, alkyl of 1–6 carbon atoms, alkoxy of 1–6 carbon atoms, halogen, trifluoromethyl;

$R^3$ and $R^4$ are each, independently, hydrogen, halogen, alkyl of 1–6 carbon atoms, aryl of 6–10 carbon atoms, trifluoromethyl, alkoxy of 1–6 carbon atoms, nitro, amino, carboalkoxy, carbamide, carbamate, urea, alkylsulfoamide, arylsulfoamide, cycloalkyl of 3–8 carbon atoms, —$NR^7(CH_2)_mCO_2H$, pyrrolidinone, a heterocycic ring having 5 to 7 atoms and having 1 to 3 heteroatoms selected from oxygen, nitrogen, or sulfur, or aryl of 6–10 carbon atoms mono-, di-, or tri-substituted with trifluoromethyl, alkyl of 1–6 carbon atoms or, alkoxy of 1–6 carbon atoms;

$R^5$ is hydrogen, alkyl of 1–6 carbon atoms, —$CH(R_8)R^9$, —$C(CH_2)_nCO_2R^{10}$, —$C(CH_3)_2CO_2CO_2R^{10}$, —$CH(R^8)(CH_2)_nCO_2R^{10}$, —$CH(R^8)C_6H_4CO_2R^{10}$ $R^6$ is alkylene of 1 to 3 carbon atoms, $R^7$ is hydrogen or alkyl of 1 to 6 carbon atoms, $R^8$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety has 1–6 carbon atoms;

Q is

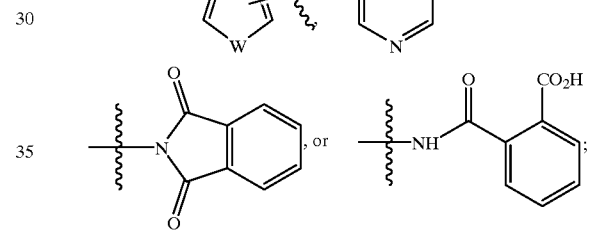

W is oxygen, sulfur, or nitrogen;
$R^9$ is —$CO_2R^{12}$, —$CONHR^{12}$, tetrazole, —$PO_3R^{12}$;
$R^{10}$ is hydrogen, alkyl of 1–6 carbon atoms, aryl of 7–15 carbon atoms, or aralkyl of 7–15 carbon atoms;
$R^{12}$ is hydrogen, alkyl, aryl of 6–12 carbon atoms, aralkyl of 7–15 carbon atoms;
m=1–3;
n=1–6;
with the proviso that when $R^1$ is halogen, Y is a bond;

or a pharmaceutically acceptable salt thereof.

71. A pharmaceutical composition which comprises a compound of formula I having the structure

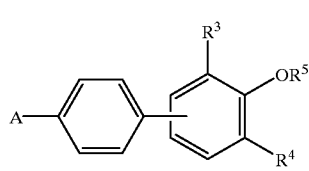

I wherein

A is

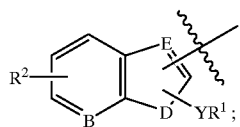

B is carbon;
D is oxygen, sulfur, or nitrogen;
E is carbon;
Y is a bond, methylene, C(O), or CH(OH);
$R^1$ is alkyl having 1 to 12 carbons, aryl of 6–12 carbon atoms, arylalkyl of 7–15 carbon atoms, halogen, carboxaldehyde, trifluoromethyl, alkoxy of 1–6 carbon atoms, 2,2-dimethyl-1,3-benzodioxole, Het-alkyl wherein the alkyl moiety have 1–6 carbon atoms, or aryl of 6–10 carbon atoms which is mono-, di-, or tri-substituted with halogen, trifluormethyl, or alkoxy of 1–6 carbon atoms;
Het is

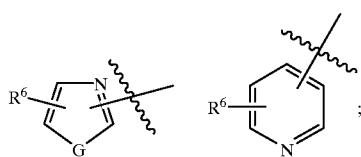

G is oxygen, sulfur or nitrogen;
$R^2$ and $R^{2a}$ are each, independently, hydrogen, alkyl of 1–6 carbon atoms, alkoxy of 1–6 carbon atoms, halogen, trifluoromethyl;
$R^3$ and $R^4$ are each, independently, hydrogen, halogen, alkyl of 1–6 carbon atoms, aryl of 6–10 carbon atoms, trifluoromethyl, alkoxy of 1–6 carbon atoms, nitro, amino, carboalkoxy, carbamide, carbamate, urea, alkylsultoamide, arylsulfoamide, cycloalkyl of 3–8 carbon atoms, $-NR^7(CH_2)_mCO_2H$, pyrrolidinone a heterocycic ring having 5 to 7 atoms and having 1 to 3 heteroatoms selected from oxygen, nitrogen, or sulfur, or aryl of 6–10carbon atoms mono-, di-, or tri-substituted with trifluoromethyl, alkyl of 1–6 carbon atoms or, alkoxy of 1–6 carbon atoms;
$R^5$ is hydrogen, alkyl of 1–6 carbon atoms, $-CH(R^8)R^9$, $-C(CH_2)_nCO_2R^{10}$, $-C(CH_3)_2CO_2R^{10}$, $-CH(R^8)(CH_2)_nCO_2R^{10}$, $-CH(R^8)C_6H_4CO_2R^{10}$
$R^6$ is alkylene of 1 to 3 carbon atoms,
$R^7$ is hydrogen or alkyl of 1 to 6 carbon atoms,
$R^8$ is hydrogen, alkyl of 1–6 carbon atoms, aryl of 6–12 carbon atoms, aralkyl of 6–12 carbon atoms, cycloalkyl of 3–8 carbon atoms, phthalic acid, or Q-alkyl wherein the alkyl moiety has 1–6 carbon atoms;
Q is

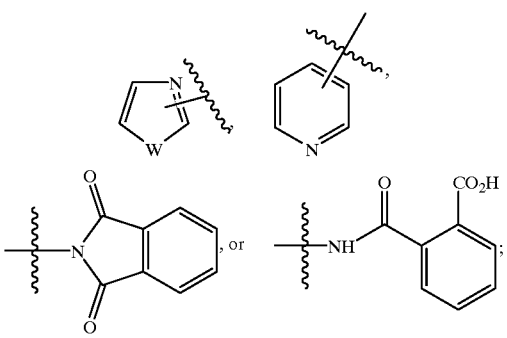

W is oxygen, sulfur, or nitrogen;
$R^9$ is $-CO_2R^{12}$, $-CONHR^{12}$, tetrazole, $-PO_3R^{12}$;
$R^{10}$ is hydrogen, alkyl of 1–6 carbon atoms, aryl of 7–15 carbon atoms, or aralkyl of 7–15 carbon atoms;
$R^{12}$ is hydrogen, alkyl, aryl of 6–12 carbon atoms, aralkyl of 7–15 carbon atoms;
m=1–3;
n=1–6;
with the proviso that when $R^1$ is halogen, Y is a bond;
or a pharmaceutically acceptable salt thereof, and a pharmaceutical carrier.

* * * * *